US008633683B2

(12) United States Patent
Yokoi et al.

(10) Patent No.: US 8,633,683 B2
(45) Date of Patent: Jan. 21, 2014

(54) APPARATUS WITH ABNORMALITY DETERMINATION FUNCTION AND METHOD FOR DETERMINING ABNORMALITY

(75) Inventors: Shoji Yokoi, Nagoya (JP); Takayuki Sakurai, Kakamigahara (JP); Tatsuya Okayama, Wako (JP); Masanobu Miki, Wako (JP); Keizo Iwama, Wako (JP); Makoto Hattori, Wako (JP); Hidetaka Ozawa, Wako (JP)

(73) Assignees: NGK Insulators, Ltd., Nagoya (JP); Honda Motor Co., Ltd., Minato-Ku (JP)

( * ) Notice: Subject to any disclaimer, the term of this patent is extended or adjusted under 35 U.S.C. 154(b) by 456 days.

(21) Appl. No.: 13/019,470

(22) Filed: Feb. 2, 2011

(65) Prior Publication Data

US 2011/0192211 A1    Aug. 11, 2011

(30) Foreign Application Priority Data

Feb. 8, 2010    (JP) .................................. 2010-025246

(51) Int. Cl.
*G01N 27/416*    (2006.01)

(52) U.S. Cl.
USPC ............. 324/72; 324/73.1; 324/522; 204/431

(58) Field of Classification Search
CPC ..... G01N 27/416; G01N 15/06; G01N 27/02; G01N 35/00; G01R 31/02; G01R 35/00; G01R 31/304
USPC .............................. 324/72.5, 73.1, 522, 713, 324/754.03–755.01; 73/1.06
See application file for complete search history.

(56) References Cited

U.S. PATENT DOCUMENTS

| 5,939,625 | A | * | 8/1999 | Torii et al. ................. 73/117.01 |
| 7,609,068 | B2 | * | 10/2009 | Ripley .......................... 324/512 |
| 2004/0164755 | A1 | * | 8/2004 | Yamaoka et al. ............. 324/754 |
| 2008/0105567 | A1 | * | 5/2008 | Okayama et al. ............. 205/775 |
| 2008/0265870 | A1 | * | 10/2008 | Nair et al. ..................... 324/105 |
| 2012/0285217 | A1 | * | 11/2012 | Duault et al. ................. 73/1.06 |

FOREIGN PATENT DOCUMENTS

| JP | 2002-365325 A1 | 12/2002 |
| JP | 2005-024518 A1 | 1/2005 |
| JP | 2009-186278 | 8/2009 |

* cited by examiner

*Primary Examiner* — Arleen M Vazquez
*Assistant Examiner* — Robert Alejnikov, Jr.
(74) *Attorney, Agent, or Firm* — Burr & Brown, PLLC

(57) ABSTRACT

The apparatus is provided with an abnormality determination means for determining abnormality of the apparatus where two different combinations of two electrodes are selected from the three electrodes, an alternating-current voltage is applied to an electrode in one combination by the voltage-applying portion to measure a value of a current flowing to the other electrode via the dielectric body by electrostatic coupling, an alternating-current voltage is applied to an electrode in another combination out of the at least two different combinations by the voltage-applying portion to measure a value of a current flowing to the other electrode via the dielectric body by electrostatic coupling, and an abnormality of the apparatus is determined from the current values measured.

6 Claims, 7 Drawing Sheets

APPARATUS WITH ABNORMALITY DETERMINATION FUNCTION AND METHOD FOR DETERMINING ABNORMALITY

BACKGROUND OF THE INVENTION

1. Field of the Invention

The present invention relates to an apparatus with an abnormality determination function and a method for determining an abnormality. More specifically, the present invention relates to an apparatus with an abnormality determination function, the apparatus being capable of easily performing a self-diagnosis of an abnormality of the electrode portion in an apparatus provided with an electrode portion having at least three electrodes and to a method for determining an abnormality to easily determine an abnormality of the electrode portion.

2. Description of Related Art

As a method for inspecting (determining) an abnormality of an apparatus provided with a substrate at least a part of which is constituted of a dielectric body and an electrode disposed on the surface or in the internal portion of the dielectric body constituting the substrate, there has been used, for example, a method where pin probes are bought into contact with both the ends of a conductive pattern (e.g., electrode). Specifically, a current is applied to one pin probe, and a voltage value is detected at the other pin probe. From the detected value, a resistance value of the conductive pattern is calculated to inspect (determine) disconnection or short circuit of the conductive pattern.

However, in such a conventional inspection method, since the pin probes have to be changed according to the damage of the conductive pattern due to the contact of the pin probes or according to the pitch of the conductive pattern, the method is very troublesome as an inspection method. Therefore, there is disclosed a method where an alternating-current signal is applied to a conductive pattern from a feed electrode subjected to capacity coupling (also referred to electrostatic coupling) with an end of the conductive pattern to detect a signal with two kinds of sensor electrodes capacity-coupled with the other end of the conductive pattern, thereby inspecting the state of the conductive pattern on the basis of the detected signal (see, e.g., JP-A-2002-365325).

In addition, as a conductive pattern inspection apparatus capable of easy inspection with high reliability, there has been suggested a conductive pattern inspection apparatus having a sensor electrode electrostatic-coupled with an end of the pattern to be inspected and a feed electrode electrostatic-coupled with the other end of the conductive pattern to detect a value of a current flowing between the power source and the sensor electrode with applying an alternating-current signal to the pattern via the feed electrode and the sensor electrode, thereby detecting presence/absence of disconnection or short circuit of a conductive pattern (see, e.g., JP-A-2005-24518).

However, the aforementioned conductive pattern inspection apparatus described in JP-A-2005-24518 has a problem of very complex constitution of the apparatus because the current value is measured by moving the sensor electrode sequentially with respect to the conductive pattern (e.g., electrode).

In addition, as the apparatus having a conductive pattern as the electrode, there is a particulate matter detection apparatus for detecting particulate matter (PM) such as soot contained in, for example, flue exhaust gas or diesel engine exhaust gas. However, since such a particulate matter detection apparatus is sometimes very small and therefore has a problem of having much difficulty in employing the constitution described in JP-A-2005-24518 from the viewpoint of the constitution of the apparatus.

SUMMARY OF THE INVENTION

The present invention has been made in view of the aforementioned problems and aims to provide an apparatus with an abnormality determination function, the apparatus being capable of easily performing self-diagnosis of an abnormality of the electrode portion in an apparatus provided with an electrode portion having at least three electrodes and a method for easily determining an abnormality of the electrode portion.

In order to achieve the aforementioned aim, the present invention provides the following apparatus with an abnormality determination function and method for determining an abnormality.

[1] An apparatus with an abnormality determination function, comprising: a substrate at least a part of which is constituted of a dielectric body, an electrode portion disposed on the surface or in the internal portion of the dielectric body constituting the substrate and having at least three electrodes, and a voltage-applying portion capable of applying an alternating-current voltage to an electrode constituting the electrode portion; wherein the apparatus is further provided with an abnormality determination means for determining abnormality of the apparatus where at least two different combinations of two electrodes are selected from the at least three electrodes, an alternating-current voltage is applied to one electrode of the two electrodes in one combination out of the at least two different combinations by the voltage-applying portion to measure a value of a current flowing to the other electrode of the one combination via the dielectric body by electrostatic coupling, an alternating-current voltage is applied to one electrode of the two electrodes in at least another combination out of the at least two different combinations by the voltage-applying portion to measure a value of a current flowing to the other electrode of the combination via the dielectric body by electrostatic coupling, and an abnormality of the apparatus is determined from the current values measured.

[2] An apparatus with an abnormality determination function according to [1], wherein the electrode portion is disposed in an exhaust system of an internal combustion engine for use, a detecting means for detecting electric characteristics of the electrode portion is further provided, and the apparatus is a particulate matter detection apparatus for detecting particulate matter contained in exhaust gas passing through the exhaust system on the basis of change of the electric characteristics due to adhesion of particulate matter in exhaust gas to the electrode.

[3] An apparatus with an abnormality determination function according to [2], wherein a removal means for removing particulate matter adhering to the electrode portion is further provided to determine an abnormality of the apparatus by the abnormality determination means after the particulate matter adhering to the electrode portion is removed by the removal means.

[4] An apparatus with an abnormality determination function according to any one of [1] to [3], wherein the substrate is an apparatus main body long in one direction and having at least one through-hole formed in one end portion, and the electrode constituting the electrode portion is constituted of at least a pair of measurement electrodes disposed on the inside surface or in the internal portion of the wall on one side of the through-hole and at least a pair of dust-collecting electrodes embedded in the internal portion of walls facing each other and forming the through-hole and outward with respect to the embedding position of the pair of measurement electrodes and covered with a dielectric body.

[5] A method for determining an abnormality of an apparatus provided with a substrate at least a part of which is constituted of a dielectric body, an electrode portion disposed on the surface or in the internal portion of the dielectric body constituting the substrate and having at least three electrodes, and a voltage-applying portion capable of applying an alternating-current voltage to an electrode constituting the electrode portion; wherein the method includes a step of determining abnormality of the apparatus where at least two different combinations of two electrodes are selected from the at least three electrodes constituting the electrode portion of the apparatus, an alternating-current voltage is applied to one electrode of the two electrodes in one combination out of the selected at least two different combinations by the voltage-applying portion to measure a value of a current flowing to the other electrode of the one combination via the dielectric body by electrostatic coupling, an alternating-current voltage is applied to one electrode of the two electrodes in at least another combination out of the least two different combinations by the voltage-applying portion to measure a value of a current flowing to the other electrode of the combination via the dielectric body by electrostatic coupling, and an abnormality of the apparatus is determined from the current values measured. constituting the electrode portion; wherein the method includes a step of determining abnormality of the apparatus where at least two different combinations of two electrodes are selected from the at least three electrodes constituting the electrode portion of the apparatus, an alternating-current voltage is applied to an electrode out of two electrodes in one combination out of the selected at least two different combinations by the voltage-applying portion to measure a value of a current flowing to the other electrode of the one combination via the dielectric body by electrostatic coupling, an alternating-current voltage is applied to an electrode out of two electrodes in at least another combination out of the least two different combinations by the voltage-applying portion to measure a value of a current flowing to the other electrode of the combination via the dielectric body by electrostatic coupling, and an abnormality of the apparatus is determined from the current values measured.

[6] A method for determining an abnormality according to [5], wherein the apparatus to be inspected is a particulate matter detection apparatus further provided with a detecting means for detecting electric characteristics of the electrode portion, and the particulate matter detection apparatus detects particulate matter contained in exhaust gas passing through the exhaust system on the basis of change of the electric characteristics due to adhesion of particulate matter in exhaust gas to the electrode portion.

[7] A method for determining an abnormality according to [6], wherein the apparatus to be inspected is further provided with a removal means for removing particulate matter adhering to the electrode portion to determine an abnormality of the apparatus after the particulate matter adhering to the electrode portion is removed by the removal means.

[8] A method for determining an abnormality according to any one of [5] to [7], wherein the substrate of the apparatus to be inspected is an apparatus main body long in one direction and having at least one through-hole formed in one end portion, and the electrode constituting the electrode portion is constituted of at least a pair of measurement electrodes disposed on the inside surface or in the internal portion of the wall on one side of the through-hole and at least a pair of dust-collecting electrodes embedded in the internal portion of walls facing each other and forming the through-hole and outward with respect to the embedding position of the pair of measurement electrodes and covered with a dielectric body.

In an apparatus with an abnormality determination function of the present invention, in an apparatus provided with an electrode portion having at least three electrodes, self-diagnosis of an abnormality of the electrode portion can be performed easily. In addition, in a method for determining an abnormality of the present invention, an abnormality of the aforementioned electrode portion having at least three electrode can easily be determined.

In the present invention, in the case that another conductor (e.g., another electrode) is disposed near a conductor (e.g., one electrode) where an alternating-current voltage is applied, the magnitude of electric current flowing between electrically independent electrodes via a dielectric body is measured by the use of a phenomenon (hereinbelow sometimes referred to as "electrostatic coupling") of induction of electric charge due to generation of floating capacitance between the conductors, thereby determining (inspecting) an abnormality of each of the electrodes. Further, a apparatus with an abnormality determination function of the present invention can not only determine (inspect) presence/absence of an abnormality, but also restrict or identify the position of the abnormality when an abnormality is determined.

That is, in the present invention, at least two different combinations of two electrodes are selected from the electrode portion having at least three electrodes, the current value of each of the at least two combinations is measured, and the measurement values are compared with each other to be able to determine an abnormality of the apparatus and further restrict or identify the portion of the abnormality.

This enables to easily conduct self-diagnosis of an abnormality of the aforementioned electrode portion. For example, even with a very small apparatus, an abnormality can be determined well. For example, in a particulate matter detection apparatus having specific constitution for detecting particulate matter in exhaust gas, whether the detection of particulate mater is performed normally or not is judged, and a damage or defect of the apparatus can be inspected well.

REFERENCE NUMERALS

1: apparatus main body, 1a: end portion on one side, 1b: end portion on the other side, 1c: tip portion on one side, 1d: tip portion on the other side, 2: through-hole, 11: dust-collecting electrode (high voltage dust-collecting electrode), 12: dust-collecting electrode (grounded dust-collecting electrode), 11a, 12a, 13a: leading terminal, 11b, 12b, 13b: wiring, 13: heating portion, 15, 16: measurement electrode, 15a, 16a: measurement electrode leading terminal, 15b, 16b: measurement electrode wiring, 21: substrate, 21a: dielectric body, 22: electrode portion, 22a, 22b, 22c: electrode, 23a, 23b, 23c: wiring, 31: voltage-applying portion, 32: abnormality determination means, 33: detection means, 34: removal means, 100: apparatus with abnormality determination function (apparatus), 100a: particulate matter detection apparatus (apparatus with abnormality determination function)

DETAILED DESCRIPTION OF THE INVENTION

Next, embodiments of the present invention will be described in detail with referring to drawings. However, the present invention is by no means limited to the following embodiments, and it should be understood that changes, improvements, and the like of the design may suitably be made on the basis of ordinary knowledge of a person of ordinary skill within the range of not deviating from the gist of the present invention.

Figure 1A:
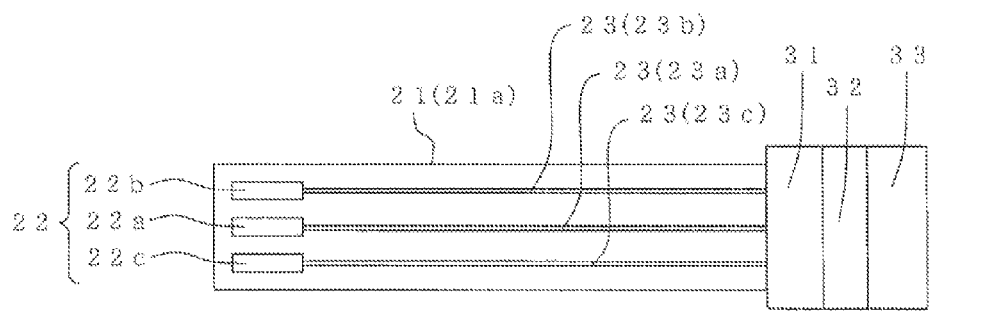
FIG. 1A is an explanatory view schematically showing an embodiment of an apparatus with an abnormality determination function of the present invention.
Figure 1B:
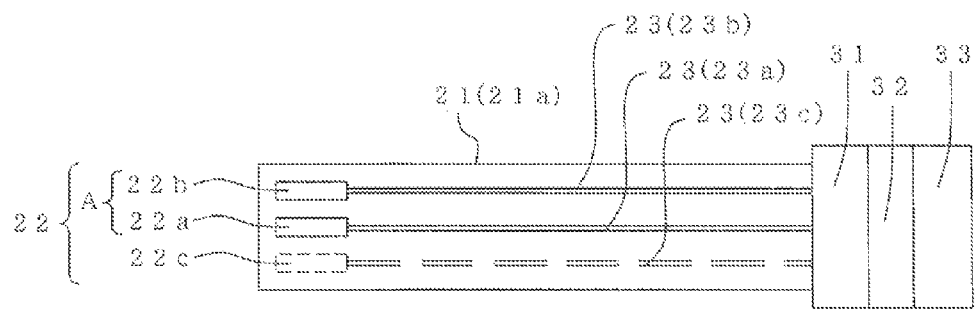
FIG. 1B is an explanatory view schematically showing an embodiment of an apparatus with an abnormality determination function of the present invention.
Figure 1C:
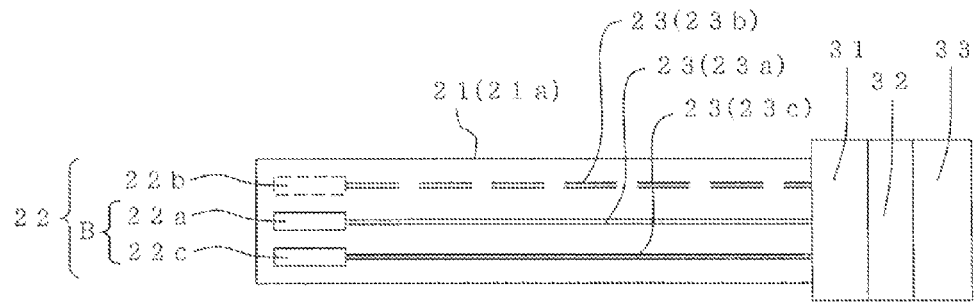
FIG. 1C is an explanatory view schematically showing an embodiment of an apparatus with an abnormality determination function of the present invention.

[1] Characteristics of an Apparatus with an Abnormality Determination Function of the Present Invention:

FIGS. 1A to 1C are explanatory views schematically showing an embodiment of an apparatus with an abnormality determination function of the present invention. Incidentally, FIG. 1B shows an example where a combination A is selected from the three electrodes, and FIG. 1C shows an example where another combination B is selected from the three electrodes. In FIGS. 1B and 1C, the electrodes not selected for the combinations are shown by broken lines.

As shown in FIGS. 1A to 1C, the apparatus 100 with an abnormality determination function of the present embodiment is an apparatus provided with a substrate 21 at least a part of which is constituted of a dielectric body 21a, an electrode portion 22 disposed on the surface or in the internal portion of the dielectric body 21a constituting the substrate 21 and having at least three electrodes 22a, 22b, 22c, and a voltage-applying portion 31 capable of applying an alternating-current voltage to an electrode (e.g., electrode 22a) constituting the electrode portion 22.

In addition, the apparatus 100 with an abnormality determination function of the present embodiment is an apparatus 100 with an abnormality determination function further provided with an abnormality determination means 32 for determining abnormality of the apparatus 100, where at least two different combinations (e.g., a combination A of electrodes 22a and 22b and another combination B of electrodes 22a and 22c) of two electrodes are selected from the at least three electrodes 22a, 22b, and 22c, an alternating-current voltage is applied to an electrode (e.g., electrode 22a) of the two electrodes 22a and 22b in the combination A out of the at least two different combinations by the voltage-applying portion 31 to measure a value of a current flowing to the other electrode (i.e., electrode 22b) of the one combination A via the dielectric body 21a by electrostatic coupling, an alternating-current voltage is applied to an electrode (e.g., electrode 22a) of two electrodes 22a and 22c in at least another combination (combination B) out of the at least two different combinations other than combination A by the voltage-applying portion 31 to measure a value of a current flowing to the other electrode (i.e., electrode 22c) of the combination (i.e., combination B) via the dielectric body 21a by electrostatic coupling, and an abnormality of the apparatus 100 is determined from the current values measured.

The apparatus with an abnormality determination function of the present embodiment is an apparatus where, in the case that another conductor (e.g., another electrode) is disposed near a conductor (e.g., one electrode) where an alternating-current voltage is applied, the magnitude of electric current flowing between electrically independent electrodes via a dielectric body is measured by the use of a phenomenon (hereinbelow sometimes referred to as "electrostatic coupling") of induction of electric charge due to generation of floating capacitance between the conductors, thereby determining (inspecting) an abnormality of each of the electrodes. Further, the apparatus with an abnormality determination function of the present embodiment can not only determine (inspect) presence/absence of an abnormality, but also restrict or identify the position of the abnormality when an abnormality is determined.

That is, in the apparatus 100 with an abnormality determination function of the present embodiment, at least two different combinations of two electrodes are selected from the electrode portion 22 having at least three electrodes 22a, 22b, and 22c, the current value of each of the at least two combinations is measured, and the measurement values are compared with each other to determine an abnormality of the apparatus. Further, the portion of the abnormality of the apparatus can be restricted or identified.

Therefore, the apparatus 100 with an abnormality determination function of the present embodiment can judge (inspect) abnormality (e.g., damage or disconnection) of the electrode portion 22 well. For example, whether the apparatus in use is functioning normally or not can be judged easily with high accuracy.

In the apparatus with an abnormality determination function of the present embodiment, there is no particular limitation on the constitution of the apparatus itself as long as it is provided with the electrode portion having at least three electrodes, and any apparatus can be employed. For example, it may be a detection apparatus for measuring electrostatic capacitance or resistance value between electrodes by electrodes constituting the electrode portion, an electronic circuit where a large number of circuit elements are incorporated in one substrate, or the like.

Examples of such an apparatus disposed inside a path where exhaust gas passes include a particulate matter detection apparatus for detecting particulate matter contained in exhaust gas, a NOx sensor for detecting NOx in exhaust gas, and the like.

The apparatus 100 with an abnormality determination function shown in FIGS. 1A to 1C is explained with respect to an example of the case of performing an abnormality determination by selecting two different combinations (i.e., one combination A and another combination B) of two electrodes out of the electrode portion 22 having three electrodes 22a, 22b, and 22c and measuring the value of the current flowing via the dielectric body 21a due to electrostatic coupling. The abnormality determination may be performed by, for example, selecting three different combinations of two electrodes from the electrode portion 22 having three electrodes 22a, 22b, and 22c and measuring the value of the current in each combination. That is, by selecting at least two combinations, the abnormality determination can be performed by comparing the current values measured, and, by increasing the number of the combinations, the abnormality determination can be performed in more detail. In addition, for example, by employing the same electrode as the one electrode of each combination in at least two combinations selected, the abnormality of the other electrode of each combination can easily be inspected.

Incidentally, though the apparatus 100 with an abnormality determination function shown in FIGS. 1A to 1C shows an example of the case where three electrodes (electrodes 22a, 22b, and 22c) constitute the electrode portion 22, there is no limitation on the number of the electrodes as long as the apparatus has the necessary number of the electrodes from the viewpoint of the constitution of the apparatus. For example, when the apparatus has four electrodes, the apparatus should be constituted to perform the aforementioned abnormality determination by selecting at least two different combinations of two electrodes from the four electrodes. In the case of four electrodes, there are six combinations of two electrodes. When the direction of applying the alternating-current voltage is taken into consideration, 12 combinations (2×6 combinations) can be considered. In such a case, by selecting at least two combinations, the abnormality determination can be performed from the current values measured. For example, when there are three or more electrodes, electrode combinations appropriate for the abnormality determination can suitably be selected from the constitution of the circuit of these electrodes. Incidentally, for example, in the case of having an electrode suspected to have an abnormality among the electrodes, by allowing two or more combinations among the selected combinations to have the electrode, the abnormality determination of the electrode can be performed in more detail.

Incidentally, there is no particular limitation on the method of combining two electrodes as long as the value of the current flowing between the electrodes can be measured by an abnormality determination means.

Incidentally, the electrodes constituting the electrode portion is of metal or alloy having conductivity and should be disposed on the surface or in the internal portion of the dielectric body constituting the substrate. Examples of the electrodes include an electrode (i.e., conductive pattern) formed by printing (e.g., screen printing) a conductive paste containing platinum (Pt), molybdenum (Mo), tungsten (W), palladium (Pd), or the like on the surface or in the internal portion of a dielectric body; and an electrode where thin plate-shaped or thin film-shaped metal is disposed on the surface or in the internal portion of a dielectric body.

In addition, as shown in FIG. 1A, the electrodes 22a, 22b, 22c constituting the electrode portion 22 are electrically connected with the voltage-applying portion 31 and the abnormality determination means 32, are constituted to be able to apply an alternating-current voltage to each of the electrodes 22a, 22b, 22c independently by the voltage-applying portion 31, and are constituted to be able to measure the current value of each of the electrodes 22a, 22b, 22c independently according to the combination of the electrodes by the abnormality determination means 32.

Incidentally, FIG. 1A shows an example of a case where the electrodes 22a, 22b, 22c are electrically connected with the voltage-applying portion 31 and the abnormality determination means 32 via the wiring 23a, 23b, 23c, respectively. For example, in the case that each of the electrodes is a conductive pattern or the like, the electrodes may electrically be connected directly with the voltage-applying portion 31 and the abnormality determination means 32 by the conductive pattern constituting the electrode.

The substrate where the aforementioned electrodes are disposed is at least partially constituted of a dielectric body, and a current is passed between the electrodes due to electrostatic coupling by applying an alternating-current voltage on an electrode of the two electrodes selected. Here, the "dielectric body" means a substance where dielectricity is more dominant over conductivity and substance serving as an insulator against a direct-current voltage.

The substrate in the apparatus with an abnormality determination function of the present embodiment can be used as a substrate for disposing electrodes or as a member constituting the main body of an apparatus. There is no particular limitation on the kind of the dielectric body, and a dielectric body of a conventionally known dielectric substance can be employed. A preferable example is at least one kind selected from the group consisting of alumina, cordierite, mullite, glass, zirconia, magnesia, and titania. Of these, alumina can suitably be employed.

The abnormality determination means is for detecting various abnormalities in the apparatus by comparing the current values measured in the at least two combinations of electrodes described above. For example, by comparing a current value measured in one combination with another current value measured in another combination to determine an abnormality from the difference between the obtained values. At this time, in the case of having disconnection of an electrode used for measurement in one combination, even if an alternating-current value is applied on the electrode, the current is not measured. In addition, for example, in the case that two electrodes used for the measurement are short circuited, a current directly passes between the electrodes besides the current due to electrostatic coupling, the current measured is very high. Generally, in the case that a current passes through a dielectric body due to electrostatic coupling, it is anticipated that a current of about 10 to 100 nA is measured in a measurement electrode where the current is measured upon applying an alternating-current voltage of 100 V with 1 kHz to one electrode. Incidentally, there is no particular limitation on the frequency of the aforementioned alternating-current voltage and the height of the voltage.

As a specific method for determining an abnormality, for example, in the case that two combinations of electrodes are selected, in the first place, the current values measured in this two combinations are compared. In the case that the current values are different, a determination that any of the electrodes has an abnormality can be made. In such a case, the electrode having an abnormality can be estimated from the difference in the current values measured and the absolute values of the currents. In addition, also by measuring the current values in new combinations or the like by changing the combinations of two electrodes or the electrode where a voltage is applied, the electrode having an abnormality can be restricted or identified.

A more specific abnormality determination method will be described with referring to a flow chart showing in FIG. 2.

Figure 2:
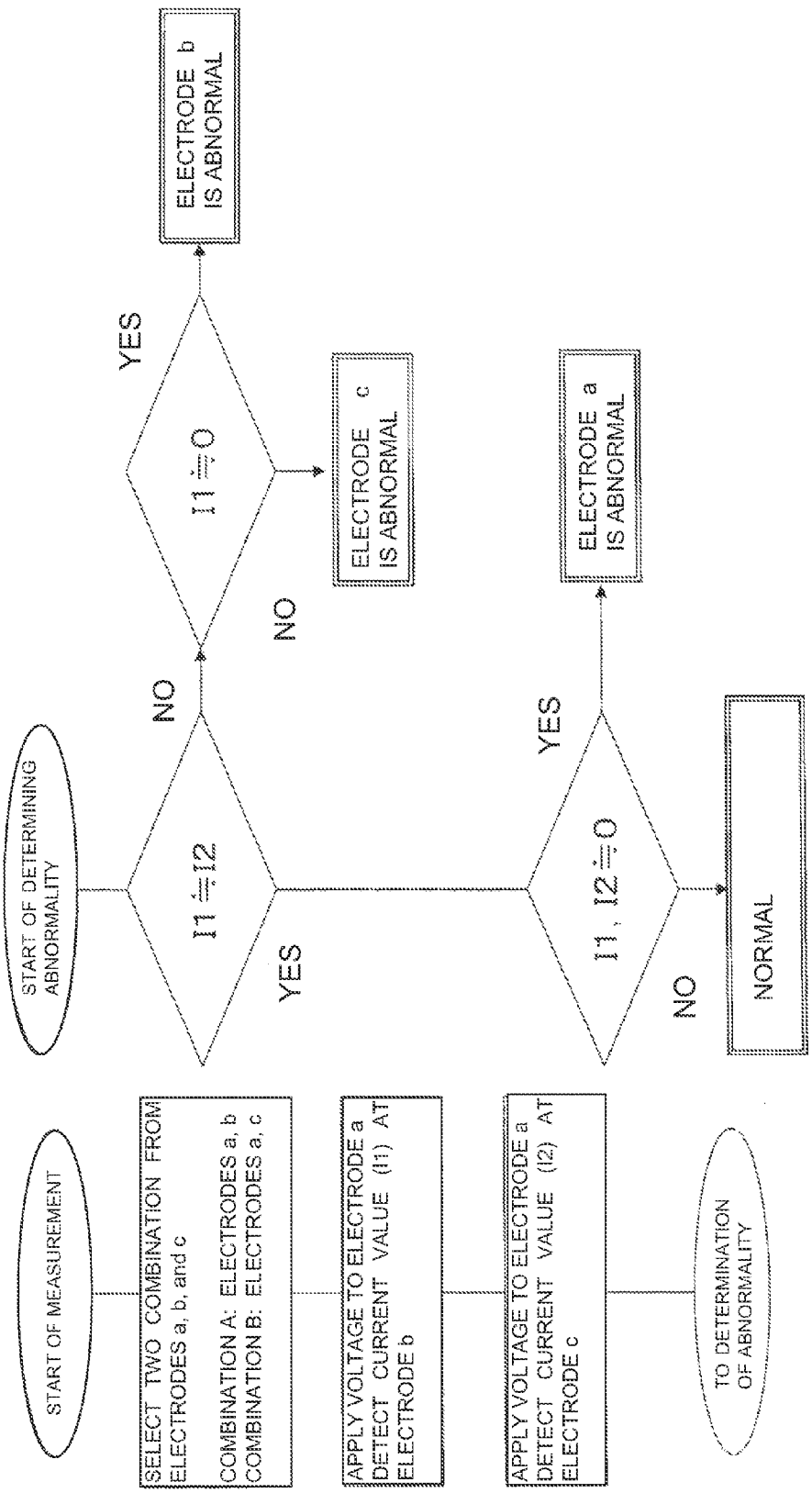
FIG. 2 is a flow chart showing an example of a method for determining an abnormality in an apparatus with an abnormality determination function of the present invention.

Here, FIG. 2 is a flowchart showing an example of an abnormality determination method in an apparatus with an abnormality determination function of the present invention.

The flowchart shown in FIG. 2 shows an example of the case where the apparatus with an abnormality determination function has three electrodes of the electrode a, electrode b, and electrode c. In the first place, two combinations of electrodes are selected from the electrode a, electrode b, and electrode c. FIG. 2 shows an example of the case of selecting the electrode a and the electrode b for the combination A and the electrode a and the electrode c for the combination B.

Next, a voltage is applied on the electrode a to detect the current value (I1) at the electrode b (combination A). In addition, in the same manner, a voltage is applied on the electrode a to detect the current value (I2) at the electrode c (combination B). Thus, abnormality determination is performed by the use of the current values (I1 and I2) measured.

In the abnormality determination, in the first place, the current value (I1) of the combination A is compared with the current value (I2) of the combination B, and the difference between the current values is confirmed (judgment of "I1 ≒ I2" of the flow chart shown in FIG. 2). When the current value (2) of the combination B is different from the current value (I1) of the combination A (e.g., the case that the difference is more than 1 nA which is a threshold value of below 1 nA), it proceeds along "no prong" of "I1 ≒ I2" judgment to confirm the value (absolute value) of the current value (I1) of the combination A (judgment of "I1 ≒ 0" in the flow chart shown in FIG. 2). When the current value (I1) is approximately zero (I1 ≒ 0) an abnormality of the electrode b is determined. When the current value (I1) is not approximately zero, an abnormality of the electrode c is determined. Incidentally, the aforementioned "approximately zero (≒ 0)" means a value in the case of below 1 nA as a threshold in current measurement. Incidentally, although 1 nA is used as the threshold in the aforementioned abnormality determination method, it is preferable to suitably set an optimal threshold value according to the constitution of the apparatus for determining an abnormality.

On the other hand, in the aforementioned judgment of "I1 ≒ I2", in the case that the current value (I1) of the combination A and the current value (I2) of the combination B is almost the same ("I1 ≒ I2"), each of the current value (I1) and the current value (I2) (absolute values) of the combination B is confirmed (judgment of "I1, I2 ≒ 0" of the flow chart shown in FIG. 2). In the case that each of the current value (I1) and the current value (I2) is approximately zero (I1, I2 ≒ 0), an abnormality of the electrode a is determined. On the other hand, each of the current value (I1) and the current value (I2) is not approximately zero, it is determined that the three electrodes of electrode a, electrode b, and electrode c subjected to abnormality determination have no abnormality (are normal).

Incidentally, the aforementioned abnormality determination method is absolutely an example, and suitable determination criteria can suitably be set according to the constitution of the apparatus, for example, material of the dielectric body where the electrodes are disposed, material and disposition interval of the electrodes, and the like. For example, in the case that the current value measured in each combination is previously known to some extent, the estimated value (estimated value of the current value measured) may be employed as the determination criterion. For example, the estimated value is "10 to 100 nA", there may be employed a determination criterion to determine that the electrode measured has an abnormality when the measured current value is below the half of the lowest estimation value (i.e., the measured current value is below 5 nA).

As a specific kind of abnormality, for example, when the measured current value is below 1 nA, at least one electrode among the electrode where measurement is performed is suspected of disconnection. However, in the case that the current value in one combination is measured, it is impossible to know which electrode between the measured electrodes (i.e., two electrodes) is disconnected. In the apparatus with an abnormality determination function of the present embodiment, since an abnormality is determined by selecting at least two combinations of electrodes, by comparing the measurement results of two combinations as in the flowchart shown in FIG. 2, the electrode having an abnormality (e.g., disconnection in this case) can be restricted or identified. For example, even in the case that the number of the electrodes is further increased, by increasing the number of combinations selected and repeating such abnormality determination, the abnormal portion can be discriminated from the normal portion or identified. In addition, examples of other kinds of abnormality include short circuit of an electrode and mixing of foreign matter, and it is possible to restrict or identify the portion having an abnormality depending on the combinations to be selected.

A measurement portion for measuring a current value in an abnormality determination means preferably can measure a current value of at least 1 nA. By employing such a measurement portion, even determination of a small abnormality in the electrode portion can be performed well. An example of such a measurement portion is the LCR meter 4263B (Trade name) of Agilent Technologies.

For example, in measurement where a current of at least 1 nA cannot be detected (i.e., measurement where the detection limit is above 1 nA), it may be difficult to measure a faint current flowing via a dielectric body due to electrostatic coupling, and it may be impossible to discriminate the case having an abnormality from the normal case. In addition, a small abnormality such as breakage of a dielectric body, a partial loss of an electrode, or the like may be overlooked.

In addition, there may be used a determination portion for determining an abnormality, which has an integrated circuit performing calculation of the difference (amount of change) between the measured current values and arithmetic processing for selecting a matching abnormality from previously set abnormality types and a display portion such as a display showing the selected abnormality.

In addition, the voltage-applying portion is a power source portion for applying a current via a dielectric body due to electrostatic coupling and preferably able to apply an alternating-current voltage of 0.1 to 1000V to an electrode in each of the at least two combinations of electrodes. For example, in the case of below 0.1V, the current measured is small, and the detection of the current may be difficult. On the other hand, when the alternating-current voltage is above 1000V, an excessive voltage is applied to the apparatus with an abnormality determination function, it may negatively affect the apparatus. Incidentally, the alternating-current voltage to be applied is more preferably 1 to 100V, particularly preferably 1 to 10V.

Incidentally, the frequency of the alternating-current voltage applied by the voltage-applying portion is preferably 1 kHz to 1 MHz, for example. By such constitution, an electric current due to electrostatic coupling is easily caused. For example, in the case of below 1 kHz, the electric current flowing between the electrodes is small, and detection may be difficult. On the other hand, in the case of above 1 MHz coupling with another wiring or the like becomes large, which may negatively affect other devices.

In addition, in the apparatus with an abnormality determination function of the present embodiment, the interval of the at least three electrodes constituting the electrode portion is preferably 50 to 500 μm, more preferably 50 to 300 μm, particularly preferably 50 to 100 μm. Such constitution enables to perform precise and stable abnormality determination. For example, when the interval between the electrodes is too small, change of a current value with respect to the change of the size due to temperature or the like may become large. In addition, when the interval between the electrodes is too wide, the value of the electric current flowing due to electrostatic coupling become small, and the measurement may become difficult. In addition, an accident error may easily be caused in the measured value or in the information obtained from the measured value.

In addition, for example, the apparatus with an abnormality determination function of the present embodiment may be provided with a temperature adjustment means for changing temperature of the dielectric body upon measurement. For example, since a dielectric body has bad insulation (i.e., since the resistance value becomes small) when temperature is high, a higher electric current flows due to electrostatic coupling. Therefore, by heating the dielectric body upon measurement, it becomes possible to measure a high current value, and an abnormality can easily be determined.

In addition, by observing the change of the current value to be measured according to the change of the temperature of the dielectric body, it is possible to inspect an abnormality which is hardly measured with single kind of temperature and an abnormality which changes (emerges) according to the temperature change. For example, in the case that the dielectric body has cracks (such as micro cracks), heating of the dielectric body causes expansion of the dielectric body to increase the interval between the micro cracks, and therefore a measured current value may have a peculiar change. By observing such a state, even an abnormality which is hardly determined in an ordinary temperature state, such as breakage (e.g., the aforementioned micro cracks) or the like of the dielectric body, can be inspected well.

Figure 3A:
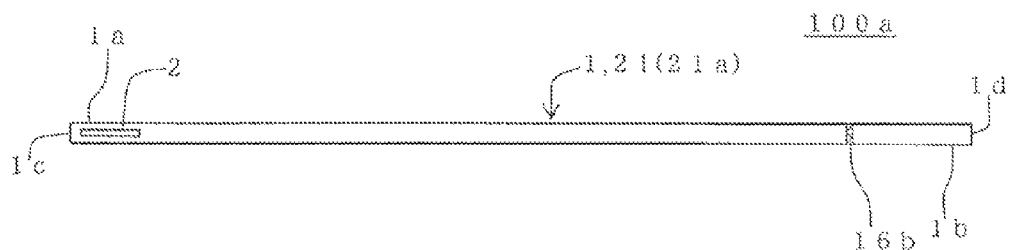
FIG. 3A is a front view schematically showing a particulate matter detection apparatus as another embodiment of an apparatus with an abnormality determination function of the present invention.
Figure 3B:
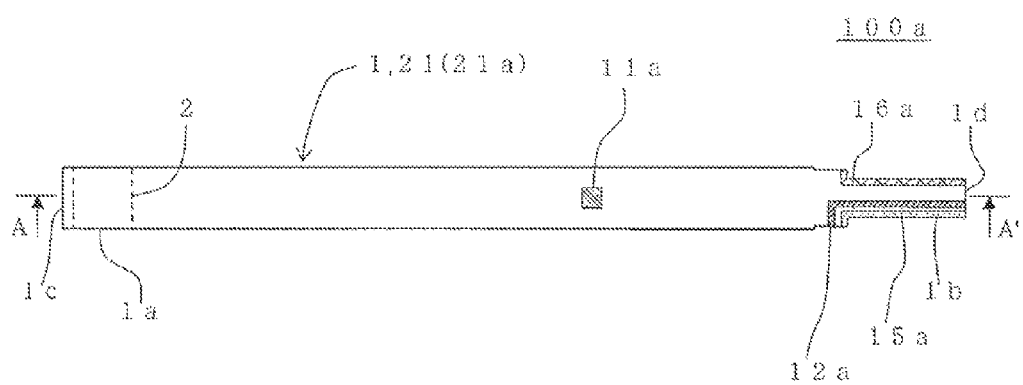
FIG. 3B is a side view showing a side face on one side of the particulate matter detection apparatus shown in FIG. 3A.
Figure 3C:
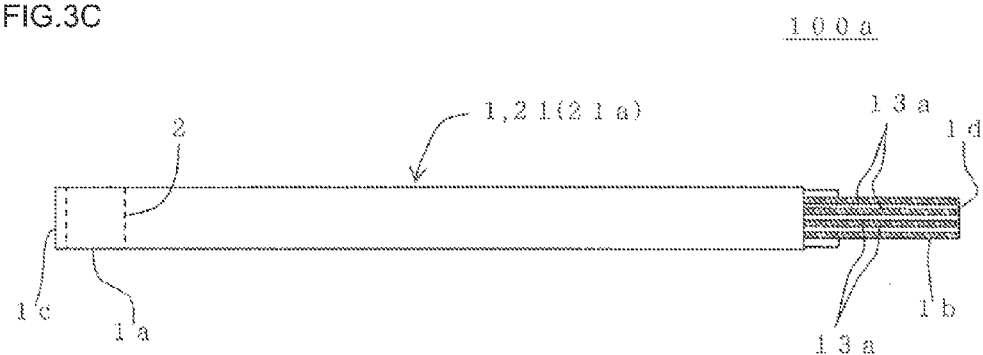
FIG. 3C is a side view showing a side face on another side of the particulate matter detection apparatus shown in FIG. 3A.
Figure 3D:
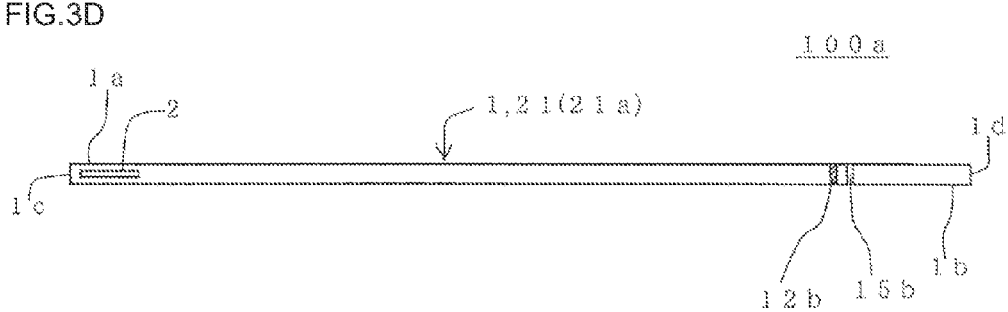
FIG. 3D is a rear view of the particulate matter detection apparatus shown in FIG. 3A.
Figure 4:
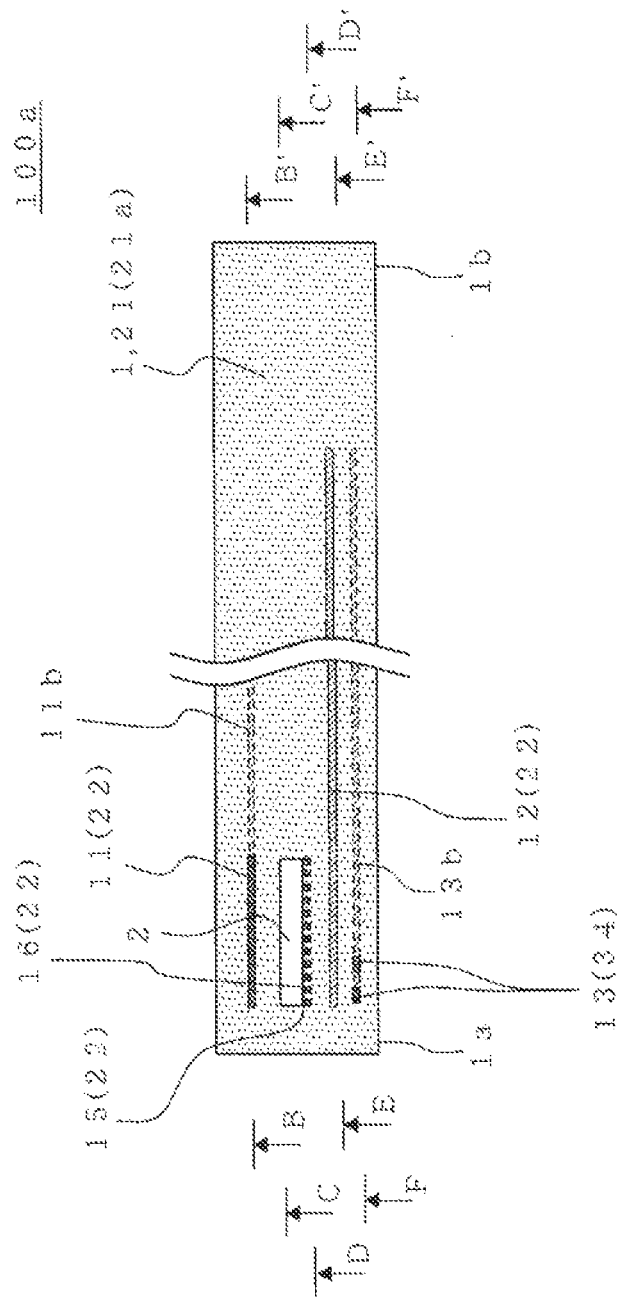
FIG. 4 is a schematic view showing the A-A' cross section of FIG. 3B.
Figure 5:
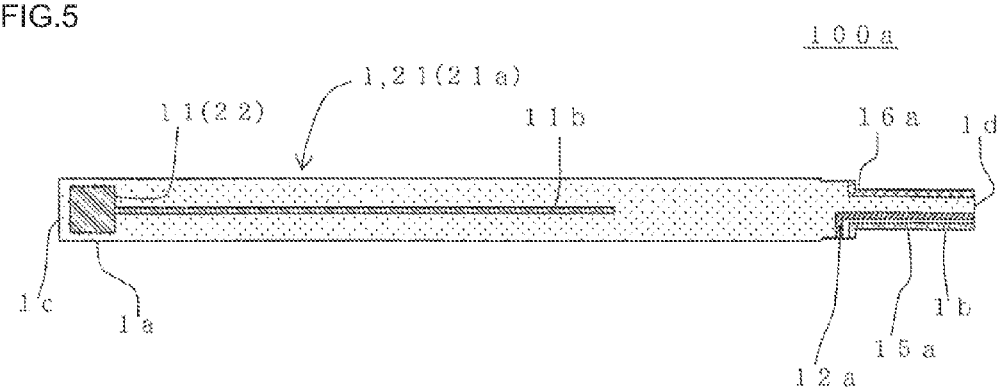
FIG. 5 is a schematic view showing the B-B' cross section of FIG. 4.
Figure 6:
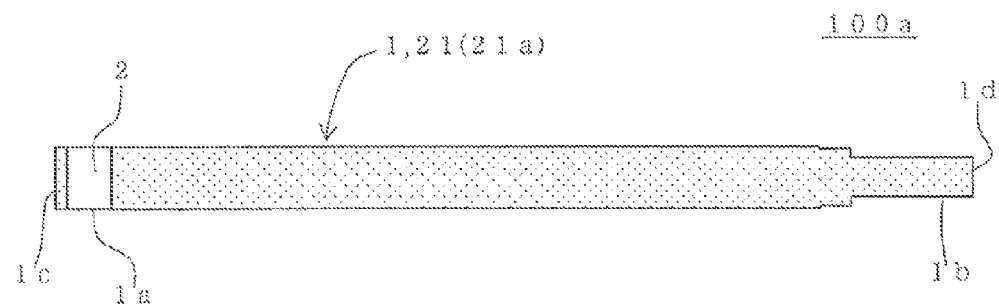
FIG. 6 is a schematic view showing the C-C' cross section of FIG. 4.
Figure 7:
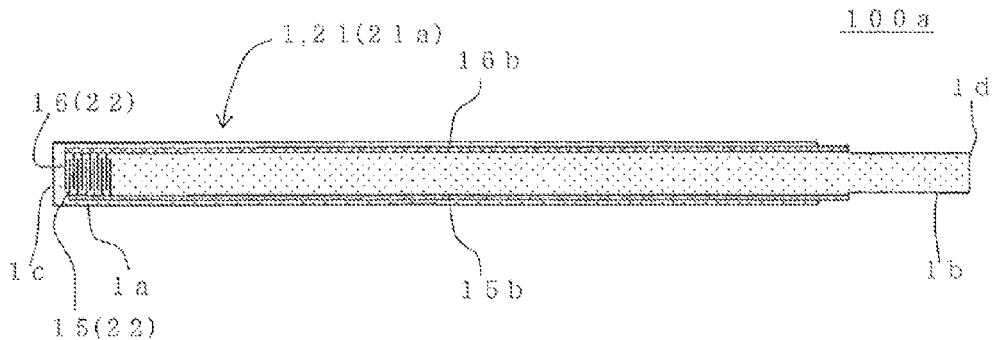
FIG. 7 is a schematic view showing the D-D' cross section of FIG. 4.
Figure 8:
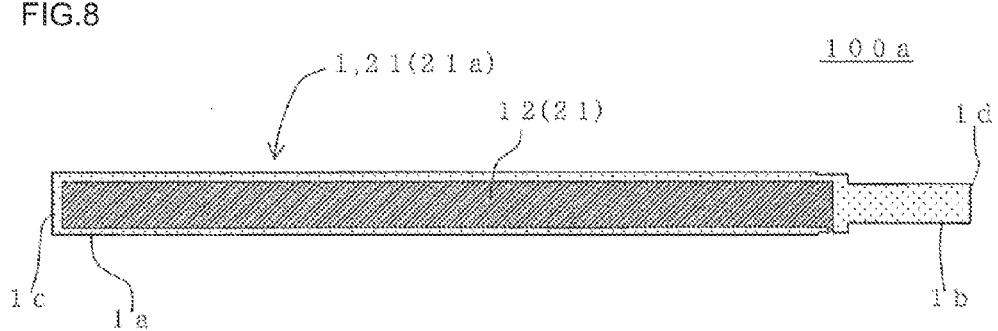
FIG. 8 is a schematic view showing the E-E' cross section of FIG. 4.
Figure 9:
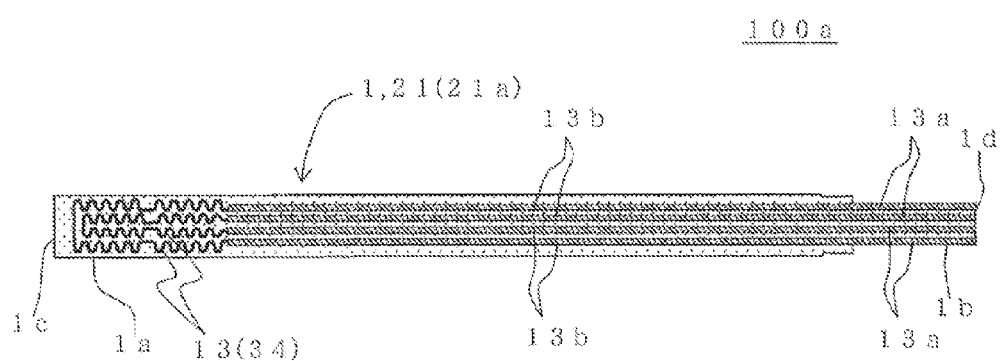
FIG. 9 is a schematic view showing the F-F' cross section of FIG. 4.

[2] Particulate Matter Detection Apparatus:

Next, as another embodiment of an apparatus with an abnormality determination function of the present invention, an example of a case that the apparatus with an abnormality determination function is a particulate matter detection apparatus for detecting particulate matter in exhaust gas will be described. FIG. 3A is a front view schematically showing a particulate matter detection apparatus as another embodiment of an apparatus with an abnormality determination function of the present invention, FIG. 3B is a side view showing a side face on one side of the particulate matter detection apparatus shown in FIG. 3A, FIG. 3C is a side view showing a side face on another side of the particulate matter detection apparatus shown in FIG. 3A, and FIG. 3D is a rear view of the particulate matter detection apparatus shown in FIG. 3A. In addition, FIG. 4 is a schematic view showing the A-A' cross section of FIG. 3B, FIG. 5 is a schematic view showing the B-B' cross section of FIG. 4, FIG. 6 is a schematic view showing the C-C' cross section of FIG. 4, FIG. 7 is a schematic view showing the D-D' cross section of FIG. 4, FIG. 8 is a schematic view showing the E-E' cross section of FIG. 4, and FIG. 9 is a schematic view showing the F-F' cross section of FIG. 4.

The particulate matter detection apparatus 100a shown in FIGS. 3A to 3D and 4 to 9 is a particulate matter detection apparatus 100a (apparatus with an abnormality determination function) provided with a substrate 21 at least a part of which is constituted of a dielectric body 21a and an electrode portion 22 which is disposed on the surface or in the internal portion of the dielectric body 21a constituting the substrate 21 and which has electrodes.

The particulate matter detection apparatus 100a is used in such a manner that the electrode portion 22 is disposed in an exhaust system of an internal combustion engine, is further provided with a detection means 33 for detecting electric characters of the electrode portion 22 as shown in FIGS. 1A to 1C, and detects particulate matter contained in exhaust gas passing through the exhaust system on the basis of the change of the electric characteristics due to adhesion of particulate matter in exhaust gas to the electrode portion 22.

In the particulate matter detection apparatus 100a shown in FIGS. 3A to 3D and 4 to 9, the substrate 21 is the apparatus main body 1 where at least one through-hole (hollow) 2 is formed in an end portion 1a on one side and which is long in one direction. The electrodes constituting the electrode portion 22 are constituted of at least a pair of measurement electrodes 15, 16 disposed on the inside surface or in the internal portion of the wall forming the through-hole 2 and at least a pair of dust-collecting electrodes 11, 12 embedded in the internal portion of walls forming the through-hole 2 and outward with respect to the embedding position of the pair of measurement electrodes 15, 16 and covered with a dielectric body 21a. Incidentally, the electrodes constituting the electrode portion 22 is not limited to the pair of measurement electrodes 15, 16 and the pair of dust-collecting element 11, 12 described above as long as there are at least three electrodes.

Further, the particulate matter detection apparatus 100a is further provided with a voltage-applying portion 31 and an abnormality determination means 32 as shown in FIGS. 1A to 1C and can determine an abnormality of the particulate matter detection apparatus 100a.

The particulate matter detection apparatus shown in FIGS. 3A to 3D and 4 to 9 is a detection apparatus where at least a pair of dust-collecting electrodes are embedded in the internal portion of the wall forming the through-hole of the apparatus main body and which can allow the measurement electrode disposed on the wall surface or on the inside surface of the wall of the through-hole to electrically adsorb charged particulate matter, and the detection apparatus measures the change of electric characteristics of the wall forming the through-hole by a pair of measurement electrodes disposed so as to face each other and can measure well the mass of the particulate matter in exhaust gas flowing into the through-hole in the exhaust gas flowing downstream of the DPF. Thus, not all the particulate matter contained in exhaust gas flowing downstream of the DPF is directly measured, but the particulate matter flowing into the through-hole is measured, and the amount of the entire particulate matter in exhaust gas can be estimated roughly on the basis of the measured value. Therefore, a slight amount of particulate matter can be measured.

Such a particulate matter detection apparatus can confirm whether a normal measurement is being performed when a detection apparatus does not receive a signal relating to the detection at all and the exhaust gas treatment apparatus functions normally, or a when the detection is not recognized until the signal is detected because the signal "not detected" is very small. This enables the particulate matter detection apparatus to easily perform confirmation of a zero point of the particulate matter detection apparatus and to confirm a defect (abnormality) such as a damage of the detection apparatus.

Incidentally, the "abnormality" in such a particulate matter detection apparatus means various defects caused in the particulate matter detection apparatus and, in particular, means that the apparatus is in a state of giving a change which should not be present by right to the electric characteristics of the electrode portion and hindering the normal measurement.

The electrode portion in the particulate matter detecting apparatus is for measuring a change of the electric characteristics according to adhesion of the particulate matter by allowing the particulate matter to adhere to the electrode portion. That is, the electrode portion is constituted of electrodes (i.e., the pair of measurement electrodes described above) used as a detection portion (sensor) of the particulate matter detection apparatus. Examples of such an electrode for the electrode portion include an electrode formed by applying a conductive paste on the surface or the like of the apparatus and an electrode constituted of an electrode or the like of a metal plate or the like. The electrode portion is electrically connected with a detection means and constituted so as to be able to detect (measure) electric characteristics in the electrode portion by a detection means. Of course, the electrode portion is electrically connected also with the voltage-applying portion and the abnormality determination means.

In addition, the electrode portion may contain, for example, an electrode for generating an electric field for collecting particulate matter contained in exhaust gas at the apparatus (i.e., the pair of dust-collecting electrodes described above) besides the electrodes for measuring the particulate matter. That is, the particulate matter detection apparatus detects particulate matter in exhaust gas from the change of electric characteristics by allowing the particulate matter in exhaust gas to adhere to the particulate matter detection apparatus (in particular, electrode portion) and reading out the change of the electric characteristics of the electrodes (measurement electrodes) constituting the electrode portion. Therefore, the apparatus may further be provided an electrode for collecting particulate matter flowing in exhaust gas (dust-collecting electrode) by, for example, generating an electric field around the particulate matter detection apparatus.

The detection means is for detecting particulate matter contained in exhaust gas by reading out the change of electric characteristics measured in the electrode portion by the particulate matter adhering around the electrode portion and the vicinity of the electrode portion. Since particulate matter contained in exhaust gas is composed mainly of soot, the particulate matter is conductive. Therefore, in the case that the particulate matter adheres to the electrode portion and the like, the particulate matter changes the electric characteristics measured. Therefore, measuring the change of electric characteristics of the electrode portion provided in the exhaust system of the internal combustion engine enables to detect whether particulate matter is contained in the exhaust gas or not.

A specific detection means is a detection portion (detection circuit) for detecting particulate matter contained in exhaust gas from the change of electric characteristics (e.g., electrostatic capacitance and resistance value) of the electrode portion. For example, in the case that electrostatic capacitance is to be measured as the electric characteristic of the electrode portion, an electrostatic capacitance is measured by the use of a LCR meter, and, when the electrostatic capacitance measured is changed, detection is performed as a voltage proportional to the electrostatic capacitance by a converter or a charge amplifier.

Incidentally, as the constitution of the portion for detecting particulate matter of the particulate matter detection apparatus, there may be employed conventionally known constitution of the detection portion of the particulate matter detection apparatus. An example of such a particulate matter detection apparatus is the particulate matter detection apparatus described in JP-A-2009-186278.

The removal means is for removing particulate matter adhering to the electrode portion. The particulate matter detecting apparatus can perform more precise abnormality determination by removing particulate matter adhering to the electrode portion by this removal means. Of course, the removal means is used for regenerating the particulate matter detection apparatus by removing the particulate matter adhering to the electrode portion to detect particulate matter well. Incidentally, it is preferable that the aforementioned removal means can remove not only the particulate matter adhering to the electrode portion, but also the particulate matter adhering to other portions of the apparatus, for example, the dielectric body where the electrode portion is disposed.

As described above, the particulate matter contained in exhaust gas is conductive, and, when particulate matter adheres to the electrode portion or the dielectric body when the value of the current flowing between electrodes due to electrostatic coupling is measured, a current may flow via the particulate matter, or a resistance value between electrodes is changed, and thereby sometimes generating a large error in the current value is measured. By removing the particulate matter adhering to the electrode portion or the dielectric body by the use of the aforementioned removal means, the influence of the particulate matter to the measurement value can be reduced, and more precise and detailed inspection can be performed.

The constitution of the removal means is not particularly limited as long as it can remove particulate matter adhering to the electrode portion, more preferably the particulate matter detection apparatus. An example of the removal means is a heater which applies heat to a portion giving a change of electric characteristics measured by the electrode portion and is able to combust and remove the adhering particulate matter. Incidentally, the removal of the particulate matter adhering to the electrode portion by a removal means may hereinbelow be referred to as "regeneration" of the particulate matter detection apparatus.

In the particulate matter detecting apparatus 100a shown in FIGS. 3A to 3D and 4 to 9, at least two different combinations of two electrodes are selected from a pair of measurement electrode 15, 16 and a pair of dust-collecting electrode 11, 12, and the value of the current flowing via the dielectric body 21a (apparatus main body 1) due to electrostatic coupling is measured to determine an abnormality of an electrode portion 22 by an abnormality determination means 32 (see FIG. 1A). Thus, by selecting at least two combinations of electrodes from the pair of measurement electrodes 15, 16 and the pair of dust-collecting electrode 11, 12, in the case that an abnormality is caused in the electrode portion 22, the portion where the abnormality is caused and the nature of the abnormality can be restricted or identified, and, in the case that the abnormality is discovered, operations of change, repair, or the like of the trouble portion (abnormal portion) can be performed easily and quickly.

As a particular example of an abnormality, in the case of disconnection or contact failure of an electrode constituting the electrode portion, for example, the measured current value becomes below half of the predicted value of the current value measured (anticipated value of the current value measured) upon measurement in a specific combination. In the case that such a measurement result is obtained, an abnormality of at least one electrode in two electrodes in the combination becomes obvious. Incidentally, the abnormality determination method may be according to the aforementioned abnormality determination method (e.g., flow chart shown in FIG. 2).

In addition, when the particulate matter detection apparatus is disposed in the exhaust system of an internal combustion engine for use, it is preferable to perform regular regeneration of the apparatus by the aforementioned removal means, and it is preferable to perform abnormality determination by the abnormality determination means in time for the regeneration of the apparatus (i.e., after the regeneration of the apparatus is performed). This enables to perform regular diagnosis of the apparatus and discover an abnormality of the apparatus in an early stage.

In addition, in the case that the particulate matter detection apparatus is disposed in the exhaust system of an automobile for use, the apparatus may be constituted in such a manner that the abnormality determination by the abnormality determination means is always performed at the onset of automobile operation. Thus, by coordinating the automobile engine start-up and the abnormality determination, in the case that the particulate matter detection apparatus has an abnormality, the abnormality can be discovered in an earlier stage.

[2-1] Constitution of Particulate Matter Detection Apparatus:

Next, the constitution of the particulate matter detection apparatus shown in FIGS. 3A to 3D and 4 to 9 will be described in more detail.

In the particulate matter detecting apparatus 100a shown in FIGS. 3A to 3D and 4 to 9, at least two different combinations (e.g., a combination of a pair of dust-collecting electrodes 11, 12 and another combination of a dust-collecting electrode 11 and a measurement electrode 15) of two electrodes are selected from four electrodes of a pair of measurement electrodes 15, 16 and a pair of dust-collecting electrodes 11, 12, an alternating-current voltage is applied to an electrode (e.g., dust-collecting electrode 11) in the two electrodes in one combination of the at least two combinations by a voltage application portion 31 (see FIG. 1A), the value of the current flowing to the other electrode (i.e., dust-collecting electrode 12) of the combination A via the dielectric body 21a due to electrostatic coupling is measured, an alternating-current voltage is applied to an electrode (e.g., dust-collecting electrode 11) in the two electrodes of another combination by the voltage-applying portion 31, the value of the current flowing to the other electrode (i.e., measurement electrode 15) in the combination via the dielectric body 21a by electrostatic coupling is measured, and an abnormality of the apparatus 100 is determined by the abnormality determination means 32 (see FIG. 1A) from the current values measured.

Of course, since the particulate matter detection apparatus 100a has four electrodes, there are six selectable combinations. Therefore, all the six combinations may be selected for the abnormality determination. In addition, in the case that the position where the abnormality is anticipated is limited to some extent because of the conditions of the apparatus, the abnormality determination may be performed by selecting the combinations predominantly containing the electrode where the abnormality is anticipated.

The abnormality such as disconnection or damage of an electrode, or short circuit, damage of the dielectric body, and the like can be inspected. By such a self-diagnosis of the particulate matter detection apparatus, it is possible to judge whether the detection of particulate matter is normally performed or not and to inspect well damages and defects of the apparatus.

Upon the abnormality determination, it is preferable to apply an alternating-current voltage of 0.1 to 1000V to perform measurement in conditions capable of detecting a current of at least 1 nA. The measurement under the aforementioned conditions enables to inspect very small defects of the particulate matter detecting apparatus, and, in the case that the particulate matter detection apparatus has some trouble (defect), the trouble can be discovered in an early stage. Incidentally, for the measurement of a current, there may be used the LCR meter 4263B (Trade name) of Agilent Technologies. Incidentally, the alternating-current voltage applied is further preferably 1 to 100V, particularly preferably 1 to 10V.

In addition, in the measurement where a current of at least 1 nA cannot be detected (i.e., measurement where the detection limit is above 1 nA), it may be difficult to measure a faint current flowing via the dielectric body due to electrostatic coupling, and discrimination of an abnormal case from a normal case may be impossible. In addition, a small defect such as breakage of a dielectric body, a partial loss of a measurement electrode, or the like may be overlooked. In a particulate matter detection apparatus, if the apparatus having even a small defect as described above is continuously used, the small defect may develop into a serious defect. Therefore, it is preferable to discover a defect in an early stage to conduct change or repair of the trouble portion.

The method for determining an abnormality can be performed in the same manner as in the abnormality determination in the aforementioned apparatus with an abnormality determination function of one embodiment. For example, in the case the current value measured as one of criteria for judgment of the abnormality determination is below 1 nA, it can be judged that at least one of the electrodes where measurement was performed has disconnection. For example, in the particulate matter detection apparatus 100a as shown in FIGS. 3A to 3D and 4 to 9, upon measuring the magnitude of the current in the other dust-collecting electrode 12 with applying an alternating-current voltage to one dust-collecting electrode 11, in the case the measured current value is below 1 nA, it can be judged that at least one of the dust-collecting electrode 11 and the dust-collecting electrode 12 has disconnection. In addition, for example, upon measuring the magnitude of the current at the measurement electrode 15 in a pair of the measurement electrodes 15, 16 with applying an alternating-current voltage to one dust collecting electrode 11, in the case that the measured current value is below 1 nA, it can be judged that at least one of the dust-collecting electrode 11 and the measurement electrode 15 has disconnection. In addition, for example, in the case that an excessive current above 1000 nA of the measured current value is flowing, it can be judged (inspected) that electrodes in the selected combination have short circuit. For example, by repeating such inspection, the abnormal portion can be discriminated from the normal portion or can be identified.

In addition, since the particulate matter detection apparatus 100a shown in FIGS. 4 and 9 has a heating portion 13 as the removal means 34, the abnormality determination may be performed during heating the dielectric body by using the heating portion 13 as the temperature adjusting means. By observing the change in temperature of the dielectric body and the current value measured, it is possible to inspect the abnormality having difficulty in measurement at fixed temperature, the abnormality whose state changes by the change of temperature, and the like.

Incidentally, since the electrostatic coupling used as a means for determining an abnormality in the present invention is more difficult to cause as the distance between the electrodes increases, it is particularly effective when it is used as a particulate matter detection means having a rather small size, for example, as an apparatus for detecting particulate matter in exhaust gas discharged from an automobile engine.

[2-2] Each Constituent of Particulate Matter Detecting Apparatus:

Next, each constituent of the particulate matter detection apparatus shown in FIGS. 3A to 3D and 4 to 9 will be described in more detail.

[2-2a] The Apparatus Main Body:

The apparatus main body is a portion long in one direction and having at least one through-hole in one end portion and functioning as a substrate of the particulate matter detection apparatus. The apparatus main body is constituted of a dielectric body, and at least a pair of dust-collecting electrodes are disposed in the internal portion of walls facing each other and forming the through-hole to generate an electric field in the through-hole by applying a voltage to the pair of dust-collecting electrodes. In addition, the particulate matter contained in a fluid flowing into the through-hole is electrically adsorbed on the wall faces of the through-hole, and the change in the electric characteristics of the walls forming the through-holes is measured by a pair of measurement electrodes, thereby detecting the mass of the particulate matter adsorbed on the wall faces of the through-hole.

The dielectric body constituting the apparatus main body is preferably made of at least one kind selected from the group of alumina, cordierite, mullite, glass, zirconia, magnesia, and titania. Of these, alumina can suitably be used. By embedding the dust-collecting electrodes in the internal portion of the apparatus main body of such a dielectric body, it is possible to form dust-collecting electrodes covered with a dielectric body. In addition, the particulate matter detection apparatus has excellent thermal durability and insulation breakdown resistant characteristics.

Incidentally, the "one end portion of the apparatus main body" means the range from the tip portion 1c on one side of the apparatus main body to the position corresponding with the length of 50% of the whole length of the apparatus main body 1. In addition, "the other end portion of the apparatus main body" means the range from the tip portion 1d on the other side of the apparatus main body to the position corresponding with the length of 50% of the whole length of the apparatus main body 1. Incidentally, the end portion on the one side of the apparatus main body is the range from the tip portion 1c on the one side of the apparatus main body to the position corresponding with the length of preferably 40%, more preferably 30%, of the whole length of the apparatus main body 1. In addition, the other end portion of the apparatus main body is the range from the tip portion 1d on the other side of the apparatus main body to the position corresponding with the length of preferably 40%, more preferably 30%, of the whole length of the apparatus main body 1. A position between the end portion 1a on the one side and the end portion 1b on the other side of the apparatus main body 1 means a portion obtained by omitting the end portion 1a on the one side and the end portion 1b on the other side from the apparatus main body 1 (see FIGS. 3A to 3C).

Since the apparatus main body is formed to be long in one direction with a through-hole 2 being formed in the end portion 1a on the one side and a pair of dust-collecting electrodes 11, 12 and a pair of measurement electrodes 15, 16 being disposed (embedded), it is possible to have a state where the through-hole 2 and each electrode (e.g., dust-collection electrode 11 and a pair of measurement electrodes 15, 16) are inserted into a pipe where the exhaust gas having high temperature flows to allow the other end portion 1b to be exposed out of the pipe. This enables the portion desirably not exposed to high temperature, such as leading terminal of each electrode to be kept in the state of being exposed to the outside of the pipe. Therefore, particulate matter can be detected with high accuracy and stability.

Incidentally, though there is no particular limitation on the length of the apparatus main body 1 in the longitudinal direction, the length is preferably capable of efficiently sampling particulate matter in exhaust gas when the apparatus main body is inserted into the exhaust gas pipe.

In addition, though there is no particular limitation on the thickness (length in the direction (thickness direction) perpendicular to both the "longitudinal direction of the apparatus main body" and "gas flowing direction") of the apparatus main body 1, for example, it is preferably about 0.5 to 3 mm. Here, the "thickness of the apparatus main body 1" means the thickness in the thickest portion in the aforementioned thickness direction. In addition, though there is no particular limitation on the length (length of gas flowing direction) in the flowing direction when exhaust gas flows in the through-hole 2, it is preferably about 2 to 20 mm. In addition, the length in the longitudinal direction of the apparatus main body 1 is preferably 10 to 100 times the thickness of the apparatus main body 1, and it is preferably 3 to 100 times the length in the gas flowing direction of the apparatus main body 1.

The shape of the apparatus main body may be a plate shape having a quadrangular cross section perpendicular to the longitudinal direction as shown in FIGS. 3A and 3D, or a stick shape having a circular or an elliptic cross section perpendicular to the longitudinal direction though the illustration is omitted. In addition, another shape may be employed as long as it has a long shape in one direction.

In the particulate matter detection apparatus 100a, there is no particular limitation on the shape and size of the through-hole 2 as long as exhaust gas can pass the through-hole 2 to measure the amount of the particulate matter. For example, the length in the longitudinal direction of the apparatus main body of the through-hole 2 is preferably about 2 to 20 mm, and the width (length in the direction perpendicular to both the longitudinal direction of the apparatus main body and the exhaust gas flowing direction) of the portion between the dust-collection electrodes 11, 12 of the through-hole 2 is preferably about 3 to 30 mm.

By specifying the size of the through-hole 2 in the aforementioned range, exhaust gas containing particulate matter can sufficiently flows in the through-hole 2, and particulate matter can effectively be adsorbed inside the through-hole 2 by the electric field generated by the dust-collecting electrodes 11, 12.

In addition, as the shape of the through-hole 2, it is preferable that at least one of the inlet portion where a fluid flows in and the outlet portion where the fluid flows out of the through-hole 2 is widely opened. By the constitution where at least one of the inlet portion where a fluid flows in and the outlet portion where the fluid flows out of the through-hole 2 is widely opened, it becomes possible to allow the exhaust gas or the like flowing in the pipe to flow into the through-hole of the particulate matter detection apparatus and to be discharged (in the case that the outlet portion is widely opened) more efficiently.

In such a particulate matter detection apparatus, the apparatus main body 1 is a lamination of a plurality of tape-shaped ceramics (ceramic sheets). Since this enables to manufacture a particulate matter detection apparatus by laminating the tape-shaped ceramic sheets with sandwiching each electrode, wiring, or the like between the ceramic sheets, a particulate matter detection apparatus can efficiently be manufactured.

[2-2b] Measurement Electrode (Electrode Portion):

The measurement electrodes functioning as the electrode portion are electrodes where at least a pair of measurement electrodes are disposed on the inside face of in the internal portion of a wall forming the through-hole for detecting particulate matter contained in exhaust gas passing through an exhaust system on the basis of the change of electric characteristic of the walls forming the through-hole, the change generating by allowing the particulate matter to be electrically adsorbed on the wall faces of the through-hole by the dust-collecting electrodes. The particulate matter detecting apparatus 100a shown in FIGS. 3A, 3B and 7 is further provided with a pair of measurement electrode wirings 15b, 16b extending from the pair of measurement electrodes 15, 16, respectively, toward the other end portion 1b of the apparatus main body 1.

Though there is no particular limitation on the shape of the measurement electrode as long as it can measure the change of the electric characteristics of the walls forming the through-hole as described above, the shape branched in a comb-like shape as shown in FIG. 7 can be employed as a suitable example. Such constitution enables more precise measurement.

There is no particular limitation on the thickness of the measurement electrode, and, for example, a thickness of 5 to 30 µm is preferable. In addition, as the material for the measurement electrode, platinum (Pt), molybdenum (Mo), tungsten (W), or the like may be employed.

With these measurement electrodes, a pair of measurement electrode wirings extending toward the other end portion of the apparatus main body are electrically connected. There is no particular limitation on the width of each of the measurement electrode wirings, and, for example, it is preferably about 0.2 to 1 mm. In addition, there is no particular limitation on the thickness of the measurement electrode wirings, and, for example, it is preferably about 5 to 30 µm. As the material for the measurement electrode wiring, platinum (Pt), molybdenum (Mo), tungsten (W), or the like may be employed.

In addition, as shown in FIGS. 3A to 3D, the pair of measurement electrodes 15, 16 of the particulate matter detection apparatus 100a have the leading terminals 15a, 16a, respectively, in the other end portion 1b of the apparatus main body 1. Measurement of the electric characteristics in the case of performing abnormality determination can be performed by these leading terminals 15a, 16a. That is, the leading terminals 15a, 16a are electrically connected with the detection means 33 for detecting particulate matter (see FIG. 1A), the voltage-applying portion 31 for applying an alternating-current voltage upon the abnormality determination (see FIG. 1A), and the abnormality determination means 32 for performing abnormality determination (see FIG. 1A), respectively.

By disposing the leading terminals 15a, 16a of the pair of electrodes 15, 16 in the end portion 1b on the other side of the apparatus main body 1, the distance between the portion where the through-hole 2 is disposed (i.e., the end portion 1a on one side) and the leading terminals 15a, 16a can be increased. Therefore, it is possible that only the end portion 1a on one side where the through-hole 2 and the like are disposed is inserted into the pipe where high temperature exhaust gas flows to allow the other end portion 1b where the leading terminals 15a, 16a are disposed to be exposed outside from the pipe. When the leading terminals 15a, 16a have high temperature, detection accuracy of the particulate matter is lowered, stable detection may become difficult, and contact failure of the electric terminals and the harness for connecting outside is generated to sometimes make measurement impossible in the case of use for a long period of time. Therefore, by exposing the leading terminals 15a, 16a outside the pipe to be in a state of not being exposed to high temperature, particulate matter can be detected with high accuracy and stability.

The leading terminals 15a, 16a disposed in the other end portion 1b of the apparatus main body 1 is preferably disposed on a side face of the other end portion 1b of the apparatus main body 1 so as to extend in the longitudinal direction as shown in FIG. 3B. Incidentally, though the other end portion 1b of the apparatus main body 1 is narrow in FIG. 3B, the end portion 1b of the apparatus main body 1 may be narrow and does not have to be narrow. There is no particular limitation on the shape and size of the leading terminals 15a, 16a. For example, it is preferably band-shaped having a width of 0.1 to 2.0 mm and a length of 0.5 to 20 mm. As the material for the leading terminals 15a, 16a, there may be employed nickel (Ni), platinum (Pt), chrome (Cr), tungsten (W), molybdenum (Mo), aluminum (Al), gold (Au), silver (Ag), or copper (Cu).

[2-2c] Dust-Collecting Electrode (Electrode Portion):

The dust-collecting electrodes functioning as the electrode portion are embedded in the internal portion of each of the walls forming the through-hole and facing each other and outward with respect to the position where the pair of measurement electrodes described above and covered with the dielectric body constituting the apparatus main body. By applying a predetermined voltage between the dust-collecting electrodes 11 and 12, an electric field can be generated in the through-hole 2.

There is no particular limitation on the shape of the dust-collecting electrodes as long as the dust-collecting electrodes are embedded in the internal portion of the walls forming the through-hole and can generate an electric field in the through-hole 2. In the particulate matter detection apparatus of the present embodiment, an electrode of the dust-collecting electrodes is a high voltage dust-collecting electrode 11 where a high voltage is applied and which is disposed inside the wall across the through-hole 2 on the opposite side of the wall where the measurement electrodes 15, 16 are disposed (see FIG. 4), and the other electrode of the dust-collecting electrodes is a grounded dust-collecting electrode 12 disposed inside the wall on the same side as the wall where the measurement electrodes 15, 16 are disposed (see FIG. 4). There is no particular limitation on the thickness of each of the dust-collecting electrodes, and, for example, it is preferably 5 to 30 µm. The material of the dust-collecting electrodes may be platinum (Pt), molybdenum (Mo), tungsten (W), or the like.

There is no particular limitation on the shape and size of the dust-collecting electrodes 11, 12 as long as an electric field can be generated in the through-hole 2. Examples of the shape include a quadrangle, a circle, and an ellipse. In addition, the size of the dust-collecting electrodes 11, 12 is preferably 70% or more of the area of the through-hole 2 viewed from the side face thereof, for example.

For example, FIG. 5 shows an example of the case where the high voltage dust-collecting electrode 11 is formed to have about the same size as the through-hole. To the high voltage dust-collecting electrode 11 is connected a wiring 11b extending in the longitudinal direction of the apparatus main body 1, and the wiring 11b is subjected to interlayer connection (via connected) to the leading terminal 11a shown in FIG. 3B in the tip (the tip on the side where it is not connected to the electrode 11) portion. The width of the wiring 11b is not particularly limited and preferably about 0.2 to 1 mm, for example. In addition, the thickness of the wiring 11b is not particularly limited and preferably about 5 to 30

μm, for example. In addition, as the material for the wiring 11b, there may be employed platinum (Pt), molybdenum (Mo), or tungsten (W).

Incidentally, though both the leading terminals of a pair of dust-collecting electrodes may be disposed in the other end portion of the apparatus main body, it is preferable, as shown in FIGS. 3A to 3D, that the leading terminal 12a of the grounded dust-collecting electrode (grounded dust-collecting electrode 12) is disposed in the other end portion 1b of the apparatus main body 1 and that the leading terminal 11a of the high voltage dust-collecting electrode 11 is disposed in a position between the end portion 1a and the other end portion 1b of the apparatus main body 1. This can dispose the leading terminal 12a of the grounded dust-collecting electrode 12 and the leading terminal 11a of the high voltage dust-collecting electrode 11 with having a space therebetween. Therefore, when a voltage is applied between the leading terminal 11a and the leading terminal 12a in order to apply a voltage between the pair of dust-collecting electrodes 11 and 12, creeping discharge can effectively be inhibited from generating on the surface of the apparatus main body 1.

In the particulate matter detection apparatus 100a, the distance between the leading terminal 11a and the leading terminal 12a is preferably 5 to 100 mm, more preferably 10 to 70 mm. When it is shorter than 5 mm, short circuit due to creeping discharge may easily be caused. On the other hand, when it is longer than 100 mm, in the case that the apparatus main body 1 of the particulate matter detection apparatus 100a is mounted in the pipe or the like in such a manner that the leading terminal 11a is located outside the pipe, the portion protruding outside the pipe of the apparatus main body 1 is too long, and attachment of the apparatus main body 1 in a narrow space may become difficult.

In addition, the distance between the leading terminal 11a disposed in the position between the end portion 1a and the other end portion 1b of the apparatus main body 1 and the through-hole 2 is preferably 10 mm or more, more preferably 20 mm or more. When it is shorter than 10 mm, when the particulate matter detection apparatus 100a is mounted in the pipe in such a manner that the portion of the through-hole 2 is inserted into the pipe, the heat of the high temperature exhaust gas flowing in the pipe may easily influence the leading terminal 11a.

There is no particular limitation on the shape and the size of the leading terminal 11a of the high voltage dust-collecting electrode 11 is not particularly limited. For example, a polygon such as a quadrangle having a width of 0.5 to 3 mm and a length of 0.5 to 3 mm is preferable. However, a circle, an ellipse, a racetrack shape or another shape may be employed. As the material for the leading terminal 11a, nickel (Ni), platinum (Pt), chrome (Cr), tungsten (W), molybdenum (Mo), aluminum (Al), gold (Au), silver (Ag), copper (Cu), stainless steel, kovar, or the like may be employed.

The distance, between the high voltage dust-collecting electrode 11 and the through-hole 2 and the distance between the grounded dust-collecting electrode 12 and the through-hole 2 are preferably 50 to 500 μm, more preferably 100 to 300 μm. A distance in such a range enables to effectively generate an electric field in the through-hole. The distance between each of the dust-collecting electrodes 11, 12 and the through-hole 2 is the thickness of the portion facing the through-hole 2 of the dielectric body covering each of the dust-collecting electrodes 11, 12.

As the condition of the electric field generated by the dust-collecting electrodes, 50 to 200 kV/cm is preferable though it changes according to the gap (distance between the pair of dust-collecting electrodes) and the gas temperature.

The particulate matter detection apparatus 100a is an apparatus where particulate matter contained in a fluid (i.e., exhaust gas) flowing in the through-hole 2 is electrically adsorbed on the wall face of the through-hole 2, and the change of electric characteristics due to the adhesion of the particulate matter is read out to detect the particulate matter contained in exhaust gas. In the case that particulate matter in exhaust gas is already charged before entering the through-hole 2, the particulate matter is adsorbed due to an electric field generated in the through-hole 2. On the other hand, in the case that the particulate matter is not charged, the particulate matter is charged by the electric field generated in the through-hole 2, and the charged particulate matter is electrically adsorbed on the wall face of the through-hole 2.

[2-2d] Detection Means:

The detection means is for detecting electric characteristics of the electrode portion. Specifically, for example, when the electric characteristic to be measured is electrostatic capacitance, the LCR meter 4263B of Agilent Technologies or the like can be employed.

In the particulate matter detection apparatus 100a shown in FIGS. 3A to 3D, the leading terminals 15a, 16a of the measurement electrodes 15, 16 are electrically connected to the detection means 33 (see FIG. 1A), and constituted to be able to detect the electric characteristics of the measurement electrodes 15, 16.

[2-2e] Heating Portion (Removal Means):

The particulate matter detection apparatus 100a shown in FIGS. 4 and 9 is provided with a heating portion 13 disposed (embedded) in the internal portion of the apparatus main body 1 along the wall face (wall face in parallel with the side face of the apparatus main body 1) of the through-hole 2. The heating portion 13 is a removal means 25 of the present invention. By heating the apparatus by the heating portion 13, the particulate matter adsorbed on the walls forming the through-hole 2 can be heated and oxidized (i.e., the apparatus can be regenerated). In addition, at the time of measurement or the like of the mass of the particulate matter, temperature of the internal space of the through-hole 2 is adjusted to be desired, and temperature for stably measuring the change of electric properties of the walls forming the through-hole 2 can be adjusted. In addition, by the use of the heating portion 13, the temperature of the apparatus main body 1, i.e., dielectric body can be changed, and the relation between the temperature of the dielectric body and the value of the current flowing due to electrostatic coupling can be inspected.

Though the heating portion 13 may have a wide film shape, it is preferable that a wire-shaped metal material is disposed in a wavelike fashion and makes a U-turn in the tip portion as shown in FIG. 9. Such a shape enables to uniformly heat the internal portion of the through-hole to remove particulate matter adhering to the electrode portion 21 (measurement electrodes 15, 16). As the material for the heating portion 13, platinum (Pt), molybdenum (Mo), tungsten (W), or the like may be employed. Though the heating portion 13 is preferably embedded in the internal portion of the apparatus main body 1 along the wall face of the through-hole 2, it may be formed not only in the position where the through-hole 2 is disposed but also in such a manner that it further extends toward the other end portion 1b side of the apparatus main body 1 as shown in FIG. 9. This enables to reduce the temperature difference between the internal portion of the through-hole and the vicinity of the through-hole to have an advantage of reducing breakage of an element (apparatus main body) caused by rapid heating. It is preferable that the heating portion can raise the temperature of the internal space of the through-hole up to 650° C.

In addition, though FIG. 9 shows an example of the case where two heating portions 13 are formed by two wirings, the heating portion may be one or three or more. In addition, though the illustration is omitted, the heating portions may be disposed on both the side walls forming the through-hole, respectively. That is, the disposition and the number of the heating portion(s) are according to the necessary disposition and the necessary number for achieving the aim such as oxidation removal of trapped particulate matter, temperature adjustment.

In addition, the heating portions 13 shown in FIG. 9 are connected to the wirings 13b, and each of the wirings 13b is subjected to interlayer connection to each of the leading terminals 13a as shown in FIG. 3C. The leading terminals 13a of the heating portions 13 are preferably disposed in the other end portion 1b of the apparatus main body 1 in order to avoid the thermal influence when the end portion 1a of the apparatus main body 1 is heated as in the case of the leading terminals 15a, 16a of the measurement electrodes 15, 16. In FIG. 3C, though the four leading terminals 13a are disposed so as to form four rows on the side surface side on the other side of the apparatus main body 1, the disposition of the leading terminals 13a is not limited to this disposition.

[2-2f] Voltage-Applying Portion:

The voltage-applying portion is for applying an alternating-current voltage to one electrode constituting the electrode portion, and it is preferable that the voltage-applying portion can apply an alternating-current voltage of 0.1 to 1000V. In addition, the frequency of the alternating-current voltage applied by the voltage-applying portion is preferably 1 kHz to 1 MHz, for example. Such a voltage-applying portion can be constituted by, for example, an electronic circuit constituted of an oscillation circuit and an output amplifier.

[2-2g] Abnormality Determination Means:

The abnormality determination means determine an abnormality of the particulate matter detecting apparatus by comparing current values measured by at least two combinations (two combinations of electrodes). Specifically, it is constituted of a measurement portion for measuring the current flowing via a dielectric body due to electrostatic coupling and a determination portion for determining an abnormality.

As the measurement portion, a portion constituted in the same manner as the detection portion of the aforementioned detection means can be used. That is, by the use of the detection portion of the detection means, the current values can be measured. For example, since the LCR meter 4263B or the like of Agilent Technologies has both the voltage-applying portion function and the measurement portion function, the measurement can be performed by using them.

In addition, as the determination portion for determining an abnormality, there may be employed a portion to have an integrated circuit where the difference of the measured current values is calculated to perform an arithmetic processing of selecting a matching abnormality from previously set abnormality types according to the difference and a display portion such as a display showing the selected abnormality.

[3] Abnormality Determination Method:

Next, an embodiment of an abnormality determination method of the present invention will be described. The abnormality determination method of the present embodiment is an abnormality determination method for inspecting (determining) an abnormality of an apparatus by performing an abnormality determination of the apparatus performed in the apparatus with an abnormality determination function (e.g., particulate matter detection apparatus).

That is, the abnormality determination method of the present embodiment is a method for determining an abnormality of an apparatus provided with a substrate at least a part of which is constituted of a dielectric body, an electrode portion disposed on the surface or in the internal portion of the dielectric body constituting the substrate and having at least three electrodes, and a voltage-applying portion capable of applying an alternating-current voltage to an electrode constituting the electrode portion; wherein the method includes a step of determining abnormality of the apparatus where at least two different combinations of two electrodes are selected from the at least three electrodes constituting the electrode portion of the apparatus, an alternating-current voltage is applied to an electrode out of two electrodes in one combination out of the selected at least two different combinations by the voltage-applying portion to measure a value of a current flowing to the other electrode of the one combination via the dielectric body by electrostatic coupling, an alternating-current voltage is applied to an electrode out of two electrodes in at least another combination out of the at least two different combinations by the voltage-applying portion to measure a value of a current flowing to the other electrode of the combination via the dielectric body by electrostatic coupling, and an abnormality of the apparatus is determined from the current values measured.

Such an abnormality determination method of the present embodiment can judge (inspect) an abnormality (e.g., damage or disconnection) of an apparatus to be inspected (in particular, electrode portion of this apparatus) well, and, for example, whether the apparatus in use at present is functioning normally or not can be judged easily with high accuracy. Incidentally, the abnormality determination method of the present embodiment is an abnormality determination method performed in the abnormality determination means in an apparatus with an abnormality determination function of the present embodiment described above. The method for selecting at least two different combinations of two electrodes, the method for applying an alternating-current voltage on one electrode out of the two electrodes, and the method for determining (restricting or identifying) an abnormality from the measured current values can be performed according to the methods described in the embodiment of apparatus with an abnormality determination function.

For example, in the abnormality determination method of the present embodiment, it is preferable that an alternating-current voltage of 0.1 to 1000V is applied on one electrode of each of the at least two combinations of electrodes to measure a current value of at least 1 nA in the other electrode in each of the at least two combinations of electrodes. By such constitution, more accurate and detailed inspection can be performed.

In addition, in the abnormality determination method of the present embodiment, it is preferable that the interval of the at least three electrodes constituting the electrode portion of the apparatus to be inspected is 50 to 500 μm.

Further, in the abnormality determination method of the present embodiment, the apparatus to be inspected is a particulate matter detection apparatus 100a for detecting an electric characteristics of the electrode portion 22 as shown in FIGS. 3A to 3D and 4 to 9, and the particulate matter detection apparatus 100a detects particulate matter contained in exhaust gas passing through an exhaust system on the basis of the change of electric characteristics due to adhesion of particulate matter in exhaust gas to the electrode portion 22.

In addition, in the case of such a particulate matter detection apparatus, it is preferable that the apparatus to be inspected (particulate matter detection apparatus) is further provided with a removal means for removing the particulate matter adhering to the electrode portion and, after the particulate matter adhering to the electrode portion is removed by the removal means, the apparatus to be inspected determines an abnormality of the apparatus. Such constitution reduces the error of the measurement value (current value) due to particulate matter and to inspect more accurately and minutely.

Incidentally, it is more preferable that the substrate of the apparatus to be inspected is an apparatus main body where at least one through-hole is formed in one end portion and which is long in one direction and that the electrodes constituting the electrode portion are constituted of at least a pair of measurement electrodes disposed on the inside surface or in the internal portion of a wall forming the through-hole and at least a pair of dust-collecting electrodes embedded in the internal portion of walls facing each other and forming the through-hole and outward with respect to the embedding position of the pair of measurement electrodes and covered with a dielectric body. That is, a particulate matter detecting apparatus shown in FIGS. 3A to 3D and 4 to 9 is disposed downstream of an exhaust gas treatment apparatus such as a DPF to make a judgment on whether exhaust gas purification, i.e., removal of particulate matter is normally performed or not by the exhaust gas treatment apparatus. In the case that the exhaust gas treatment apparatus is normally functioning, particulate matter is not detected as a matter of course, and it is general that an electric signal or the like which should be detected when particulate matter is detected is not detected.

However, such a particulate matter detection apparatus for measuring the "fact that particulate matter is not detected" may show the same behavior as in the case that the exhaust gas treatment apparatus is normally functioning even in the case that a signal at the time of detecting particulate matter cannot be recognized due to a defect or the like of the apparatus. Therefore, there is increased need to determine whether the particulate matter detection apparatus is normally functioning or not before and during the use of the particulate matter detection apparatus.

For example, in such a particulate matter detection apparatus, in the case that disconnection or damage of a measurement electrode, short circuit of a pair of measurement electrodes, damage of the dielectric body, or the like is caused, detection of particulate matter cannot be performed normally to overlook discharge of particulate matter or to have a large error in a quantitative measurement value. In addition, even if the measurement electrodes are normal, in the case that a dust-collecting electrode has a defect, since particulate matter contained in exhaust gas cannot be adsorbed electrically on the wall faces of the through-holes, the particulate matter passes through the through-hole together with a gas flow, and therefore particulate matter cannot be measured quantitatively.

The abnormality determination method of the present embodiment enables to confirm whether a normal measurement is being performed or not at present in a particulate matter detection apparatus which does not receive a signal relating to the detection at all in the case that the exhaust gas treatment apparatus functions normally or a detection apparatus where the detection is not recognized until the signal is detected because a signal of "not detected" is received but very small.

EXAMPLE

Here, the present invention will more specifically be described with referring to Examples. However, the present invention is by no means limited to these Examples.

(Manufacture of Apparatus with an Abnormality Determination Function)

As an apparatus with an abnormality determination function of the present invention, there was manufactured a particulate matter detection apparatus 100a as shown in FIGS. 3A to 3D and 4 to 9. Incidentally, the particulate matter detection apparatus 100a is provided with the voltage-applying portion 31, the abnormality determination means 32, and the detection means 33 shown in FIG. 1A.

As the manufacture method of the particulate matter detection apparatus 100a, in the first place, alumina was used as a raw material for the dielectric body, and polyvinylbutyral as the binder, di-2-ethylhexyl phthalate as the plasticizer, sorbitan trioleate as the dispersant, and organic solvent (xylene: butanol=6:4 (mass ratio)) as the dispersion medium were put in an alumina pot and mixed to prepare slurried forming raw material for manufacturing a green sheet. The ratio of the raw materials used were 7 parts by mass of the binder, 3.5 parts by mass of the plasticizer, 1.5 parts by mass of the dispersant, and 100 parts by mass of the organic solvent with respect to 100 parts by mass of alumina.

Next, the slurried forming raw material for manufacturing a green sheet was defoamed by stirring under reduced pressure to have a viscosity of 4 Pa·s. The viscosity of slurry was measured with a B type viscometer.

Next, the slurried raw material obtained in the aforementioned method was formed into a sheet shape by the use of a doctor blade. At this time, a cut portion-forming green sheet was also formed so that a through-hole could be formed when the green sheets were laminated. The thickness of the green sheets was 50 μm for the green sheet where a measurement electrode is disposed and 250 μm for the other green sheets.

On the surface of the green sheets obtained above were formed each of the electrodes (measurement electrodes and dust-collecting electrodes), the heating portion, the wirings, and each of the leading terminals. The conductive paste for forming each of the electrodes, grounded electrode, wirings, and attachment terminal was prepared by adding, to a platinum powder, 2-ethylhexanol as a solvent, polyvinylbutyral as the binder, di-2-ethylhexyl phthalate as the plasticizer, sorbitan trioleate as the dispersant, alumina as the common material of the green sheets, and a glass frit as a sintering auxiliary, followed by sufficiently kneading with a stone mill machine and a triroll mill (mass ratio of platinum:alumina:glass frit: 2-ethylhexanol:polyvinylbutyral:di-2-ethylhexyl phthalate: sorbitan trioleate=80:15:5:50:7:3.5:1).

In addition, the conductive paste for forming the heating portion was prepared by adding, to a platinum powder, 2-ethylhexanol as a solvent, polyvinylbutyral as the binder, di-2-ethylhexyl phthalate as the plasticizer, sorbitan trioleate as the dispersant, alumina as the common material of the green sheets, and a glass frit as a sintering auxiliary, followed by sufficiently kneading with a stone mill machine and a triroll mill (mass ratio of platinum:alumina:glass frit:2-ethylhexanol:polyvinylbutyral di-2-ethylhexyl phthalate:sorbitan trioleate=80:15:5:50:7:3.5:1).

The conductive paste formed in such a manner was printed on the surfaces of the green sheets by screen printing to form electrodes and the like having predetermined shapes. Specifically, a dust-collecting electrode is disposed on a surface on each of two green sheets out of a plurality of green sheets, and a wiring extending toward the other end portion is disposed regarding the high voltage dust-collecting electrode to form two green sheets each having a dust-collecting electrode disposed thereon.

Further, a pair of comb-shaped measurement electrodes were formed in a portion where a through-hole is formed of a green sheet having a thickness of 50 μm. The pair of comb-shaped measurement electrodes were disposed to face each other at wide intervals in such a manner that the pitch between wires of the comb teeth portion was 0.35 mm (clearance between the comb teeth was 0.15 mm, and the width of each of the comb teeth was 0.20 mm).

Further, a cutting portion for forming a through-hole in a position overlapping the measurement electrodes upon being put on the measurement electrode disposition green sheet was formed in another green sheet to form a cutting portion formation green sheet. Further, a heating portion was formed in a position overlapping the cutting portion functioning as the through-hole upon being put on the cutting portion formation green sheet was formed on still another green sheet, and a wiring extending from the heating portion toward the other end portion was disposed to form a heating portion formation green sheet.

In addition, a green sheet where no other electrode or the like is disposed is superimposed on each of the two dust-collecting electrode disposition green sheets so that the dust-collecting electrodes and the wiring were covered with the green sheet to obtain a dust-collecting electrode-embedded green sheet. The measurement electrode disposition green sheet and the cutting portion formation green sheet were sandwiched between two dust-collecting electrode-embedded green sheets, and the heating portion formation green sheet was laminated outside on the dust-collecting electrode-embedded green sheet to form a green sheet laminate body where the cutting portion was sandwiched between two dust-collecting electrodes and where the measurement electrode was sandwiched between two wirings. Each of the wirings and a leading terminal corresponding with the wiring were subjected to interlayer connection (via connection) by an embedding method of a conductive paste.

The green sheets were laminated under pressure by the use of a monoaxial pressing machine capable of heating the green sheets to obtain an unfired body of a particulate matter detection apparatus of a green sheet laminate body.

The green sheet laminate body (unfired body of a particulate matter detection apparatus) obtained above was dried at 120° C. and fired at 1500° C. to manufacture a particulate matter detection apparatus. The thus manufactured particulate matter detection apparatus was employed as the detection apparatus (1). The detection apparatus (1) was electrically connected to LCR meter (4263B (Trade name) of Agilent Technologies) as the detection means and the abnormality determination means by the use of a wiring. In addition, as the voltage-applying portion, a voltage-applying portion built into the LCR meter was used.

In addition, as particulate matter detection apparatuses to be tested, there were manufactured a detection apparatus (2) where one measurement electrode has disconnection, a detection apparatus (3) where the dust-collecting electrode on the other side (grounded dust-correcting electrode) had disconnection, and a detection apparatus (4) where the high voltage dust-collecting electrode and the one measurement electrode were short circuited besides the aforementioned particulate matter detection apparatus.

Example 1

The abnormality determination by the abnormality determination means was performed with the aforementioned detection apparatus (1). In the first place, two combinations (one combination was defined as "combination A", while the other combination was defined as "combination B") were selected from the measurement electrodes and the dust-collecting electrodes by the abnormality determination means. Specifically, the combination of the high voltage dust-collecting electrode and the one measurement electrode was defined as the combination A, and the combination of the high voltage dust-collecting electrode and the other measurement electrode was defined as the combination B.

Next, in the combination A, an alternating-current voltage of 1 kHz and 100V was applied to the high voltage dust-collecting electrode to measure a current value flowing in the one measurement electrode selected for the combination A. The current value was 57 nA. Next, the same measurement was performed for the combination B. That is, in the combination B, an alternating-current voltage of 1 kHz and 100V was applied to the high voltage dust-collecting electrode to measure a current value flowing in the measurement electrode selected for the combination B. The current value was 63 nA.

Since the magnitude of the currents measured was almost the same (error was ±5%) and included in the range of 10 to 100 nA (this range is an estimated normal range), the selected electrodes could be determined as normal. In addition, independently, the conditions of the detection apparatus (1) were confirmed in detail to find no defect.

Example 2

The aforementioned detection apparatus (2) was inspected in the same manner as in Example 1. Since the current value of the combination A was 0 nA, disconnection was suspected in one of the high voltage dust-collecting electrode and the measurement electrode. However, since the current value of the combination B was 60 nA (i.e., "not≑0") and close to the normal value to be fundamentally expected, the high voltage dust-collecting electrode was normal, and, from the current value of the combination A, it could be judged as disconnection of the measurement electrode.

Example 3

The aforementioned inspection apparatus (3) was measured in the same conditions as Example 1 with defining the combination of the dust-collecting electrode and the one measurement electrode as the combination A and the combination of the dust-collecting electrode and the other measurement electrode as the combination B. As a result, the current value of the combination A was 0 nA, and the current value of the combination B was 0 nA. Therefore, it was judged that at least the dust-collecting electrode included in both the combinations had disconnection.

Next, in order to judge abnormality of the one measurement electrode and the other measurement electrode other than the dust-collecting electrode, the combination of the high voltage dust-collecting electrode and the one measurement electrode was determined as the combination A, and the combination of the high voltage dust-collecting electrode and the other measurement electrode was determined as the combination B to perform measurement in the same conditions as in Example 1. The current value of the combination A was 57 nA, and the current value of the combination B was 63 nA. No abnormality was confirmed in the one measurement electrode and the other measurement electrode. From the results, it could be judged that the detection apparatus (3) had disconnection of a dust-collecting electrode.

Example 4

In the aforementioned detection apparatus (4), the combination of the high voltage dust-collecting electrode and the one measurement electrode was defined as the combination A, and the combination of the high voltage dust-collecting electrode and the other measurement electrode was defined as the combination B to perform measurement in the same conditions as in Example 1. As the results, the current value of combination A was 3000 nA, and the current value of the combination B was 63 nA. In the combination A, since an excessive current which would not flow due to electrostatic coupling was flowing, it could be judged that short circuit of the high voltage dust-collecting electrode and the one measurement electrode was caused.

(Result)

In an apparatus with an abnormality determination function of the present invention, by measuring the magnitude of the electric current flowing via the dielectric body due to electrostatic coupling, abnormality of a particulate matter detection apparatus could be inspected. In particular, by two combinations of elements selected, the position where an abnormality is caused and the content of the abnormality could be restricted or specified.

An apparatus with an abnormality determination function of the present invention can be used as an apparatus capable of easily performing self-diagnosis of an abnormality of the electrode portion in an apparatus provided with an electrode portion having at least three electrodes. In addition, an abnormality determination method of the present invention can easily perform abnormality determination of an apparatus provided with an electrode portion having at least three electrodes.

What is claimed is:

1. An apparatus with an abnormality determination function, comprising:
   a substrate at least a part of which is constituted of a dielectric body,
   an electrode portion disposed on the surface or in the internal portion of the dielectric body constituting the substrate and having at least three electrodes, and
   a voltage-applying portion capable of applying an alternating-current voltage to an electrode constituting the electrode portion;
   wherein the apparatus is further provided with an abnormality determination means for determining abnormality of the apparatus where at least two different combinations of two electrodes are selected from the at least three electrodes, an alternating-current voltage is applied to an electrode of two electrodes in one combination out of the at least two different combinations by the voltage-applying portion to measure a value of a current flowing to the other electrode of the one combination via the dielectric body by electrostatic coupling, an alternating-current voltage is applied to an electrode of two electrodes in at least another combination out of the at least two different combinations by the voltage-applying portion to measure a value of a current flowing to the other electrode of the combination via the dielectric body by electrostatic coupling, and an abnormality of the apparatus is determined from the current values measured;
   wherein the substrate is an apparatus main body long in one direction and having at least one through-hole formed in one end portion, and the electrode constituting the electrode portion is constituted of at least a pair of measurement electrodes disposed on the inside surface or in the internal portion of the wall on one side of the through-hole and at least it pair of dust-collecting electrodes embedded in the internal portion of walls facing each other and forming the through-hole and outward with respect to the embedding position of the pair of measurement electrodes and covered with a dielectric body.

2. An apparatus with an abnormality determination function according to claim 1, wherein the electrode portion is disposed in an exhaust system of an internal combustion engine for use, a detecting means for detecting electric characteristics of the electrode portion is further provided, and the apparatus is a particulate matter detection apparatus for detecting particulate matter contained in exhaust gas passing through the exhaust system on the basis of change of the electric characteristics due to adhesion of particulate matter in exhaust gas to the electrode.

3. An apparatus with an abnormality determination function according to claim 2, wherein a removal means for removing particulate matter adhering to the electrode portion is further provided to determine an abnormality of the apparatus by the abnormality determination means after the particulate matter adhering to the electrode portion is removed by the removal means.

4. A method for determining an abnormality of an apparatus provided with a substrate at least a part of which is constituted of a dielectric body, an electrode portion disposed on the surface or in the internal portion of the dielectric body constituting the substrate and having at least three electrodes, and a voltage-applying portion capable of applying an alternating-current voltage to an electrode constituting the electrode portion; the method comprising: selecting at least two different combinations of two electrodes from the at least three electrodes constituting the electrode portion of the apparatus; applying an alternating-current voltage to one electrode of two electrodes in one combination of the at least two different combinations of two electrodes by the voltage-applying portion and measuring a first current value of a current flowing in the other electrode of the one combination via the dielectric body by electrostatic coupling; applying an alternating-current voltage to one electrode of two electrodes in at least another combination of the at least two different combinations of two electrodes by the voltage-applying portion and measuring a second current value of a current flowing in the other electrode of the combination via the dielectric body by electrostatic coupling; and determining whether an abnormality of the apparatus exists from at least the first and second current values measured;
   wherein the substrate of the apparatus to be inspected is an apparatus main body long in one direction and having at least one through-hole formed in one end portion, and the electrode constituting the electrode portion is constituted of at least a pair of measurement electrodes disposed on the inside surface or in the internal portion of the wall on one side of the through-hole and at least it of dust-collecting electrodes embedded in the internal portion of walls facing each other and forming the through-hole and outward with respect to the embedding position of the pair of measurement electrodes and covered with a dielectric body.

5. A method for determining an abnormality according to claim 4, wherein the apparatus to be inspected is a particulate matter detection apparatus further provided with a detecting means for detecting electric characteristics of the electrode portion, and the particulate matter detection apparatus detests particulate matter contained in exhaust gas passing through the exhaust system on the basis of change of the electric characteristics due to adhesion of particulate matter in exhaust gas to the electrode portion.

6. A method for determining an abnormality according to claim 5, wherein the apparatus to be inspected is further provided with a removal means for removing particulate matter adhering to the electrode portion to determine an abnormality of the apparatus after the particulate matter adhering to the electrode portion is removed by the removal means.

\* \* \* \* \*